US012788073B2

(12) United States Patent
Moloney et al.

(10) Patent No.: US 12,788,073 B2
(45) Date of Patent: Nov. 10, 2026

(54) USER FEEDBACK SYSTEM AND METHOD

(71) Applicant: NICOVENTURES TRADING LIMITED, London (GB)

(72) Inventors: Patrick Moloney, London (GB); Juan Esteban Paz Jauregui, London (GB); Justin Han Yang Chan, London (GB); Catalin Mihai Balan, London (GB); Johanna Kuenzel, London (GB); Laziz Turakulov, London (GB); Gulben Karlidag, London (GB); Flavio Macci, London (GB)

(73) Assignee: Nicoventures Trading Limited, London (GB)

( * ) Notice: Subject to any disclaimer, the term of this patent is extended or adjusted under 35 U.S.C. 154(b) by 517 days.

(21) Appl. No.: 18/003,007

(22) PCT Filed: Jun. 14, 2021

(86) PCT No.: PCT/GB2021/051471
§ 371 (c)(1),
(2) Date: Dec. 22, 2022

(87) PCT Pub. No.: WO2021/260344
PCT Pub. Date: Dec. 30, 2021

(65) Prior Publication Data
US 2023/0284708 A1 Sep. 14, 2023

(30) Foreign Application Priority Data
Jun. 22, 2020 (GB) ...................................... 2009482

(51) Int. Cl.
*A24F 40/60* (2020.01)
*A24F 40/51* (2020.01)
(Continued)

(52) U.S. Cl.
CPC .............. *A24F 40/60* (2020.01); *A24F 40/51* (2020.01); *A24F 40/53* (2020.01); *A24F 40/65* (2020.01);
(Continued)

(58) Field of Classification Search
CPC .......... A24F 40/20; A24F 40/51; A24F 40/53; A24F 40/60; A24F 40/65
See application file for complete search history.

(56) References Cited

U.S. PATENT DOCUMENTS

| | | | | |
|---|---|---|---|---|
| 10,653,187 | B1 * | 5/2020 | Doyle | A24F 40/57 |
| 2009/0326509 | A1 * | 12/2009 | Muse | A61M 37/00 604/503 |

(Continued)

FOREIGN PATENT DOCUMENTS

| | | | | |
|---|---|---|---|---|
| CN | 204147375 U | * | 2/2015 | A24B 15/167 |
| CN | 205922886 U | | 2/2017 | |

(Continued)

OTHER PUBLICATIONS

International Search Report and Written Opinion of International Application No. PCT/GB2021/051471 on Sep. 9, 2021, all enclosed pages cited.

(Continued)

*Primary Examiner* — Vincent H Tran
(74) *Attorney, Agent, or Firm* — Burr & Forman

(57) ABSTRACT

A user feedback system for a user of a delivery device within a delivery ecosystem includes a sensor platform comprising at least a first sensor operable to detect at least a first physical property associated with at least one of user behavior other than inhalation and user physiology other than in relation to inhalation; an obtaining processor adapted to output data based upon the or each detected physical property as all or part of a user factor indicative of a user state; and an
(Continued)

estimation processor adapted to identify a corresponding feedback action expected to alter a state of the user as indicated at least in part by the or each detected physical property.

35 Claims, 5 Drawing Sheets

(51) Int. Cl.

| | |
|---|---|
| ***A24F 40/53*** | (2020.01) |
| ***A24F 40/65*** | (2020.01) |
| ***A61B 5/11*** | (2006.01) |
| ***A61B 5/16*** | (2006.01) |
| ***G16H 20/10*** | (2018.01) |

(52) U.S. Cl.
CPC ............ *A61B 5/1101* (2013.01); *A61B 5/165* (2013.01); *G16H 20/10* (2018.01)

(56) References Cited

U.S. PATENT DOCUMENTS

| | | | | |
|---|---|---|---|---|
| 2010/0081957 | A1 | 4/2010 | Hyde et al. | |
| 2012/0291791 | A1 | 11/2012 | Pradeep | |
| 2015/0257445 | A1* | 9/2015 | Henry, Jr. | A24F 40/50 131/328 |
| 2016/0057811 | A1* | 2/2016 | Alarcon | H05B 1/0227 219/494 |
| 2016/0219932 | A1* | 8/2016 | Glaser | A24F 40/485 |
| 2019/0000147 | A1* | 1/2019 | Koc | A24F 40/65 |
| 2019/0167927 | A1* | 6/2019 | Dagnello | G06N 20/00 |
| 2019/0357598 | A1* | 11/2019 | Qiu | A61B 5/682 |
| 2019/0387796 | A1* | 12/2019 | Cohen | A61M 11/042 |
| 2020/0367570 | A1* | 11/2020 | Batista | A24F 40/57 |
| 2021/0298635 | A1* | 9/2021 | Addison | A61B 5/0077 |
| 2022/0016364 | A1* | 1/2022 | Kilger | A24F 40/30 |
| 2022/0095974 | A1* | 3/2022 | Southern | A61B 5/7278 |
| 2022/0110372 | A1* | 4/2022 | Bessant | A24F 40/20 |
| 2022/0183385 | A1* | 6/2022 | Yilmaz | A24F 40/53 |
| 2022/0369714 | A1* | 11/2022 | Butin | A24F 40/53 |
| 2023/0232907 | A1* | 7/2023 | Moloney | A24F 40/65 131/329 |
| 2023/0240380 | A1* | 8/2023 | Moloney | A61M 11/00 131/328 |
| 2023/0248073 | A1* | 8/2023 | Moloney | A24F 40/60 131/328 |
| 2023/0371610 | A1* | 11/2023 | Moloney | G16H 20/10 |
| 2023/0397660 | A1* | 12/2023 | Decker | A24F 40/46 |

FOREIGN PATENT DOCUMENTS

| | | | |
|---|---|---|---|
| JP | 2020513241 | A | 5/2020 |
| KR | 20200011961 | A | 2/2020 |
| WO | 2020099824 | A1 | 5/2020 |
| WO | 2020104379 | A1 | 5/2020 |

OTHER PUBLICATIONS

Engish Translation of Office Action issued in corresponding Russian Patent Application No. 2022133698 mailed Oct. 14, 2024, all pages cited in its entirety.
Request for the Submission of an Opinion from the corresponding Korean Application No. 10-2022-7044545, mailed Jun. 24, 2025, all pages cited in its entirety.
Notice of Reasons for Refusal from corresponding Japanese Application No. 2024-208893, mailed Sep. 1, 2026, all pages cited in its entirety.

* cited by examiner

USER FEEDBACK SYSTEM AND METHOD

CROSS-REFERENCE TO RELATED APPLICATIONS

The present application is a National Phase entry of PCT Application No. PCT/GB2021/051471, filed Jun. 14, 2021, which claims priority from Great Britain Application No. 2009482.7, filed Jun. 22, 2020, each of which is hereby fully incorporated herein by reference.

TECHNICAL FIELD

The present disclosure relates to a user feedback system and method for a user of a delivery device.

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Aerosol provision systems are popular with users as they enable the delivery of active ingredients (such as nicotine) to the user in a convenient manner and on demand.

As an example of an aerosol provision system, electronic cigarettes (e-cigarettes) generally contain a reservoir of a source liquid containing a formulation, typically including nicotine, from which an aerosol is generated, e.g. through heat vaporization. An aerosol source for an aerosol provision system may thus comprise a heater having a heating element arranged to receive source liquid from the reservoir, for example through wicking/capillary action. Other source materials may be similarly heated to create an aerosol, such as botanical matter, or a gel comprising an active ingredient and/or flavoring. Hence more generally, the e-cigarette may be thought of as comprising or receiving a payload for heat.

While a user inhales on the device, electrical power is supplied to the heating element to vaporize the aerosol source (a portion of the payload) in the vicinity of the heating element, to generate an aerosol for inhalation by the user. Such devices are usually provided with one or more air inlet holes located away from a mouthpiece end of the system. When a user sucks on a mouthpiece connected to the mouthpiece end of the system, air is drawn in through the inlet holes and past the aerosol source. There is a flow path connecting between the aerosol source and an opening in the mouthpiece so that air drawn past the aerosol source continues along the flow path to the mouthpiece opening, carrying some of the aerosol from the aerosol source with it. The aerosol-carrying air exits the aerosol provision system through the mouthpiece opening for inhalation by the user.

Usually an electric current is supplied to the heater when a user is drawing/puffing on the device. Typically, the electric current is supplied to the heater, e.g. resistance heating element, in response to either the activation of an airflow sensor along the flow path as the user inhales/draw/puffs or in response to the activation of a button by the user. The heat generated by the heating element is used to vaporize a formulation. The released vapor mixes with air drawn through the device by the puffing consumer and forms an aerosol. Alternatively or in addition, the heating element is used to heat but typically not burn a botanical such as tobacco, to release active ingredients thereof as a vapor/aerosol.

How the user interacts with the e-cigarette (for example the amount of vaporized/aerosolized payload consumed by the user, and/or their pattern of use), and their actual or perceived utility from the interaction, may be influenced by the user's state, which at least in part may be expressed colloquially as their mood(s) and/or subjective need(s).

Consequently it would be useful to provide a delivery mechanism that was more responsive to the user's state.

SUMMARY

In a first aspect, a user feedback system for a user of a delivery device within a delivery ecosystem is provided.

In another aspect, a user feedback method for a user of a delivery device within a delivery ecosystem is provided.

Further respective aspects and features of the disclosure are defined in the appended claims.

It is to be understood that both the foregoing general summary of the disclosure and the following detailed description are indicative, but are not restrictive, of the disclosure.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
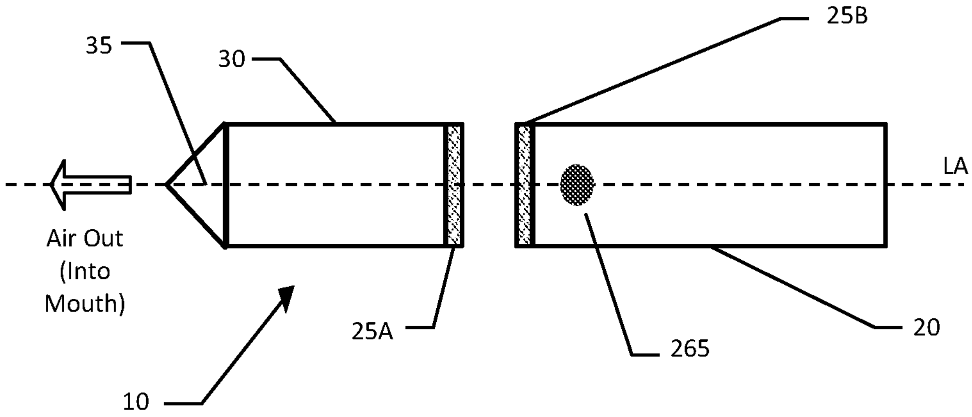
FIG. 1 is a schematic diagram of a delivery device in accordance with embodiments of the description.

A user feedback system and method is disclosed. In the following description, a number of specific details are presented in order to provide a thorough understanding of the embodiments of the present disclosure. It will be apparent, however, to a person skilled in the art that these specific details need not be employed to practice embodiments of the present disclosure. Conversely, specific details known to the person skilled in the art are omitted for the purposes of clarity where appropriate.

As described above, the present disclosure relates to a user feedback system. This user feedback system is for improving the responsiveness of a delivery device for a user.

The term 'delivery device' may encompass systems that deliver a least one substance to a user, and include non-combustible aerosol provision systems that release compounds from an aerosol-generating material without combusting the aerosol-generating material, such as electronic cigarettes, tobacco heating products, and hybrid systems to generate aerosol using a combination of aerosol-generating materials; and aerosol-free delivery systems that deliver the at least one substance to a user orally, nasally, transdermally or in another way without forming an aerosol, including but not limited to, lozenges, gums, patches, articles comprising inhalable powders, and oral products such as oral tobacco which includes snus or moist snuff, wherein the at least one substance may or may not comprise nicotine.

The substance to be delivered may be an aerosol-generating material or a material that is not intended to be aerosolized. As appropriate, either material may comprise one or more active constituents, one or more flavors, one or more aerosol-former materials, and/or one or more other functional materials.

Currently, the most common example of such a delivery device is an aerosol provision system (e.g. a non-combustible aerosol provision system) or electronic vapor provision system (EVPS), such as an e-cigarette. Throughout the following description the term "e-cigarette" is sometimes used but this term may be used interchangeably with delivery device except where stated otherwise or where context indicates otherwise. Similarly the terms 'vapor' and 'aerosol' are referred to equivalently herein.

Generally, the electronic vapor/aerosol provision system may be an electronic cigarette, also known as a vaping device or electronic nicotine delivery device (END), although it is noted that the presence of nicotine in the aerosol-generating (e.g. aerosolizable) material is not a requirement. In some embodiments, a non-combustible aerosol provision system is a tobacco heating system, also known as a heat-not-burn system. An example of such a system is a tobacco heating system. In some embodiments, the non-combustible aerosol provision system is a hybrid system to generate aerosol using a combination of aerosol-generating materials, one or a plurality of which may be heated. Each of the aerosol-generating materials may be, for example, in the form of a solid, liquid or gel and may or may not contain nicotine. In some embodiments, the hybrid system comprises a liquid or gel aerosol-generating material and a solid aerosol-generating material. The solid aerosol-generating material may comprise, for example, tobacco or a non-tobacco product. Meanwhile in some embodiments, the non-combustible aerosol provision system generates a vapor/aerosol from one or more such aerosol-generating materials.

Typically, the non-combustible aerosol provision system may comprise a non-combustible aerosol provision device and an article (otherwise referred to as a consumable) for use with the non-combustible aerosol provision system. However, it is envisaged that articles which themselves comprise a means for powering an aerosol generating component (e.g. an aerosol generator such as a heater, vibrating mesh or the like) may themselves form the non-combustible aerosol provision system. In one embodiment, the non-combustible aerosol provision device may comprise a power source and a controller. The power source may be an electric power source or an exothermic power source. In one embodiment, the exothermic power source comprises a carbon substrate which may be energized so as to distribute power in the form of heat to an aerosolizable material or heat transfer material in proximity to the exothermic power source. In one embodiment, the power source, such as an exothermic power source, is provided in the article so as to form the non-combustible aerosol provision. In one embodiment, the article for use with the non-combustible aerosol provision device may comprise an aerosolizable material.

In some embodiments, the aerosol generating component is a heater capable of interacting with the aerosolizable material so as to release one or more volatiles from the aerosolizable material to form an aerosol. In one embodiment, the aerosol generating component is capable of generating an aerosol from the aerosolizable material without heating. For example, the aerosol generating component may be capable of generating an aerosol from the aerosolizable material without applying heat thereto, for example via one or more of vibrational, mechanical, pressurization or electrostatic means.

In some embodiments, the aerosolizable material may comprise an active material, an aerosol forming material and optionally one or more functional materials. The active material may comprise nicotine (optionally contained in tobacco or a tobacco derivative) or one or more other non-olfactory physiologically active materials. A non-olfactory physiologically active material is a material which is included in the aerosolizable material in order to achieve a physiological response other than olfactory perception. The aerosol forming material may comprise one or more of glycerine, glycerol, propylene glycol, diethylene glycol, triethylene glycol, tetraethylene glycol, 1,3-butylene glycol, erythritol, meso-Erythritol, ethyl vanillate, ethyl laurate, a diethyl suberate, triethyl citrate, triacetin, a diacetin mixture, benzyl benzoate, benzyl phenyl acetate, tributyrin, lauryl acetate, lauric acid, myristic acid, and propylene carbonate. The one or more functional materials may comprise one or more of flavors, carriers, pH regulators, stabilizers, and/or antioxidants.

In some embodiments, the article for use with the non-combustible aerosol provision device may comprise aerosolizable material or an area for receiving aerosolizable material. In one embodiment, the article for use with the non-combustible aerosol provision device may comprise a mouthpiece. The area for receiving aerosolizable material may be a storage area for storing aerosolizable material. For example, the storage area may be a reservoir. In one embodiment, the area for receiving aerosolizable material may be separate from, or combined with, an aerosol generating area.

Alternatively or in addition to aerosol provision systems, a delivery device may include any device that causes/enables the introduction of an active ingredient into the body of the user in a manner that allows the active ingredient to take effect.

Example delivery devices may thus for example include a device that disperses an aerosol into a receptacle, after which a user may take the receptacle from the device and inhale or sip the aerosol. Hence the delivery device does not necessarily have to be directly engaged with by the user at the point of consumption.

In this regard, a delivery device may alternatively or in addition provide a reminder or usage regime for a user, for example reminding a user when to use a snus pouch, or other active deliverable such as a pill. The delivery device may optionally store and dispense such consumables according to the reminder or usage regime.

Similarly, an example delivery device may be a home refill station, which mixes e-liquid components for the user and uses the mix to fill a reservoir of their e-cigarette, thereby determining the type, blend, and/or concentration of active ingredients that the user will consume, all else being equal. Such a home refill station may be referred to as a 'dock', as may a power recharging station, or a device that combines both functions.

In this regard, a delivery device operating as a vending machine may similarly provide consumable refills or disposable devices based on mixes and/or selections of e-liquid components, either mixed on demand or equivalently selected from a range of pre-prepared mixes. Similarly, in other implementations, the vending machine may dispense oral products (such as for example snus, snuff, gums, gels, sprays, and other delivery systems such as patches) or other consumable products containing active ingredients and/or flavorants, for example.

In each case, the delivery device is operable to influence one or more of the amount, timing, type, blend, and/or concentration of active ingredient consumed by the user.

Hence more generally a delivery device is operable to influence a property of an active ingredient consumed by a user.

It will be appreciated that several delivery devices may operate in tandem to provide this influence. For example a home refill station, or a vending machine, may operate in conjunction with an e-cigarette to actually deliver a modification of active ingredient, or other feedback, to a user. Similarly a mobile phone may operate in parallel with an e-cigarette to provide information or analysis relevant to the modification or other feedback.

In this sense a delivery device may actually be a delivery system comprising multiple devices operating sequentially and/or in parallel to affect the desired influence/feedback. Hence references to a delivery device or delivery system herein may be considered interchangeable except where stated otherwise.

Referring now to the drawings, wherein like reference numerals designate identical or corresponding parts throughout the several views, FIG. 1 is a schematic diagram of a vapor/aerosol provision system such as an e-cigarette 10 (not to scale), providing a non-limiting example of a delivery device in accordance with some embodiments of the disclosure.

The e-cigarette has a generally cylindrical shape, extending along a longitudinal axis indicated by dashed line LA, and comprises two main components, namely a body 20 and a cartomizer 30. The cartomizer includes an internal chamber containing a reservoir of a payload such as for example a liquid comprising nicotine, a vaporizer (such as a heater), and a mouthpiece 35. References to 'nicotine' hereafter will be understood to be merely an example and can be substituted with any suitable active ingredient. References to 'liquid' as a payload hereafter will be understood to be merely an example and can be substituted with any suitable payload such as botanical matter (for example tobacco that is to be heated rather than burned), or a gel comprising an active ingredient and/or flavoring. The reservoir may be a foam matrix or any other structure for retaining the liquid until such time that it is required to be delivered to the vaporizer. In the case of a liquid/flowing payload, the vaporizer is for vaporizing the liquid, and the cartomizer 30 may further include a wick or similar facility to transport a small amount of liquid from the reservoir to a vaporizing location on or adjacent the vaporizer. In the following, a heater is used as a specific example of a vaporizer. However, it will be appreciated that other forms of vaporizer (for example, those which utilize ultrasonic waves) could also be used and it will also be appreciated that the type of vaporizer used may also depend on the type of payload to be vaporized.

The body 20 includes a re-chargeable cell or battery to provide power to the e-cigarette 10 and a circuit board for generally controlling the e-cigarette. When the heater receives power from the battery, as controlled by the circuit board, the heater vaporizes the liquid and this vapor is then inhaled by a user through the mouthpiece 35. In some specific embodiments the body is further provided with a manual activation device 265, e.g. a button, switch, or touch sensor located on the outside of the body.

The body 20 and cartomizer 30 may be detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector 25B on the body 20 that is used to connect to the cartomizer 30 also serves as a socket for connecting a charging device (not shown) when the body 20 is detached from the cartomizer 30. The other end of the charging device may be plugged into a USB socket to re-charge the cell in the body 20 of the e-cigarette 10. In other implementations, a cable may be provided for direct connection between the electrical connector 25B on the body 20 and a USB socket.

The e-cigarette 10 is provided with one or more holes (not shown in FIG. 1) for air inlets. These holes connect to an air passage through the e-cigarette 10 to the mouthpiece 35. When a user inhales through the mouthpiece 35, air is drawn into this air passage through the one or more air inlet holes, which are suitably located on the outside of the e-cigarette. When the heater is activated to vaporize the nicotine from the cartridge, the airflow passes through, and combines with, the generated vapor, and this combination of airflow and generated vapor then passes out of the mouthpiece 35 to be inhaled by a user. Except in single-use devices, the cartomizer 30 may be detached from the body 20 and disposed of when the supply of liquid is exhausted (and replaced with another cartomizer if so desired).

It will be appreciated that the e-cigarette 10 shown in FIG. 1 is presented by way of example, and various other implementations can be adopted. For example, in some embodiments, the cartomizer 30 is provided as two separable components, namely a cartridge comprising the liquid reservoir and mouthpiece (which can be replaced when the liquid from the reservoir is exhausted), and a vaporizer comprising a heater (which is generally retained). As another example, the charging facility may connect to an additional or alternative power source, such as a car cigarette lighter.

Figure 2:
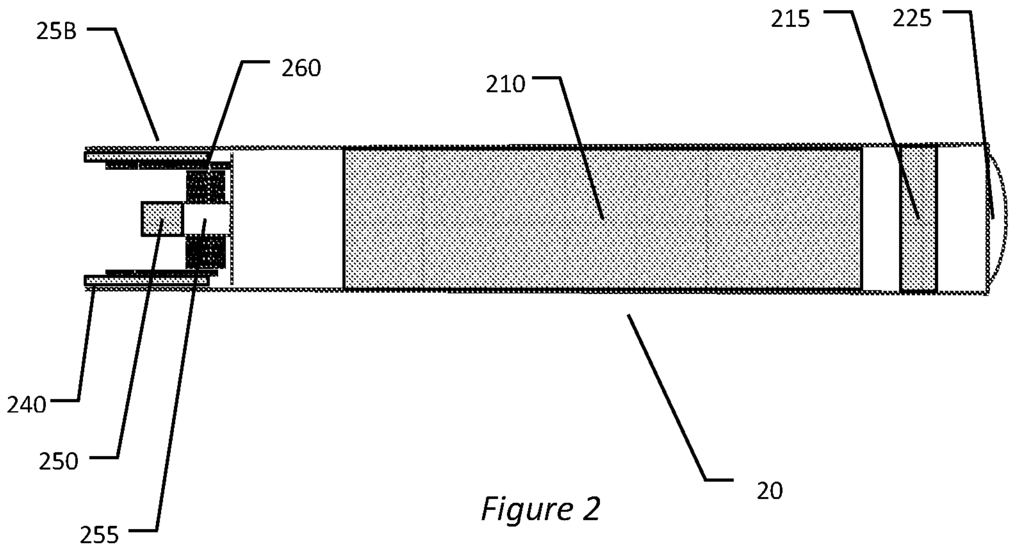
FIG. 2 is a schematic diagram of a body of a delivery device in accordance with embodiments of the description.

FIG. 2 is a schematic (simplified) diagram of the body 20 of the e-cigarette 10 of FIG. 1 in accordance with some embodiments of the disclosure. FIG. 2 can generally be regarded as a cross-section in a plane through the longitudinal axis LA of the e-cigarette 10. Note that various components and details of the body, e.g. such as wiring and more complex shaping, have been omitted from FIG. 2 for reasons of clarity.

The body 20 includes a battery or cell 210 for powering the e-cigarette 10 in response to a user activation of the device. Additionally, the body 20 includes a control unit (not shown in FIG. 2), for example a chip such as an application specific integrated circuit (ASIC) or microcontroller, for controlling the e-cigarette 10. The microcontroller or ASIC includes a CPU or micro-processor. The operations of the CPU and other electronic components are generally controlled at least in part by software programs running on the CPU (or other component). Such software programs may be stored in non-volatile memory, such as ROM, which can be integrated into the microcontroller itself, or provided as a separate component. The CPU may access the ROM to load and execute individual software programs as and when required. The microcontroller also contains appropriate communications interfaces (and control software) for communicating as appropriate with other devices in the body 10.

The body 20 further includes a cap 225 to seal and protect the far (distal) end of the e-cigarette 10. Typically there is an air inlet hole provided in or adjacent to the cap 225 to allow air to enter the body 20 when a user inhales on the mouthpiece 35. The control unit or ASIC may be positioned alongside or at one end of the battery 210. In some embodiments, the ASIC is attached to a sensor unit 215 to detect an inhalation on mouthpiece 35 (or alternatively the sensor unit 215 may be provided on the ASIC itself). In either case, the sensor unit 215, with or without the ASIC, may be understood as an example of a sensor platform. An air path is provided from the air inlet through the e-cigarette, past the airflow sensor 215 and the heater (in the vaporizer or cartomizer 30), to the mouthpiece 35. Thus when a user inhales on the mouthpiece of the e-cigarette, the CPU detects such inhalation based on information from the airflow sensor 215.

At the opposite end of the body 20 from the cap 225 is the connector 25B for joining the body 20 to the cartomizer 30. The connector 25B provides mechanical and electrical connectivity between the body 20 and the cartomizer 30. The connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The electrical contact 250 is mounted on a coil spring 255. When the body 20 is attached to the cartomizer 30, the connector 25A on the cartomizer 30 pushes against the electrical contact 250 in such a manner as to compress the coil spring in an axial direction, i.e. in a direction parallel to (co-aligned with) the longitudinal axis LA. In view of the resilient nature of the spring 255, this compression biases the spring 255 to expand, which has the effect of pushing the electrical contact 250 firmly against connector 25A of the cartomizer 30, thereby helping to ensure good electrical connectivity between the body 20 and the cartomizer 30. The body connector 240 and the electrical contact 250 are separated by a trestle 260, which is made of a non-conductor (such as plastic) to provide good insulation between the two electrical terminals. The trestle 260 is shaped to assist with the mutual mechanical engagement of connectors 25A and 25B.

As mentioned above, a button 265, which represents a form of manual activation device 265, may be located on the outer housing of the body 20. The button 265 may be implemented using any appropriate mechanism which is operable to be manually activated by the user—for example, as a mechanical button or switch, a capacitive or resistive touch sensor, and so on. It will also be appreciated that the manual activation device 265 may be located on the outer housing of the cartomizer 30, rather than the outer housing of the body 20, in which case, the manual activation device 265 may be attached to the ASIC via the connections 25A, 25B. The button 265 might also be located at the end of the body 20, in place of (or in addition to) cap 225.

Figure 3:
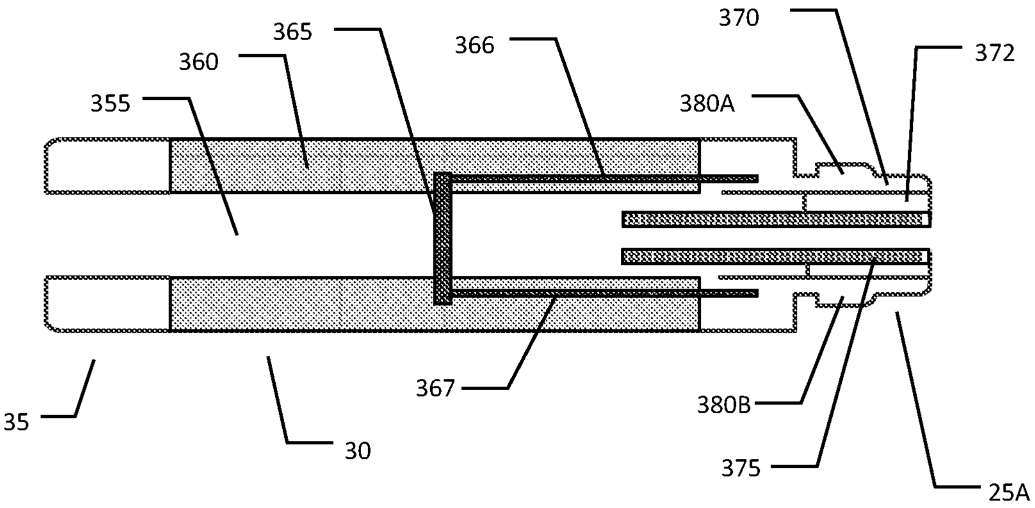
FIG. 3 is a schematic diagram of a cartomizer of a delivery device in accordance with embodiments of the description.

FIG. 3 is a schematic diagram of the cartomizer 30 of the e-cigarette 10 of FIG. 1 in accordance with some embodiments of the disclosure. FIG. 3 can generally be regarded as a cross-section in a plane through the longitudinal axis LA of the e-cigarette 10. Note that various components and details of the cartomizer 30, such as wiring and more complex shaping, have been omitted from FIG. 3 for reasons of clarity.

The cartomizer 30 includes an air passage 355 extending along the central (longitudinal) axis of the cartomizer 30 from the mouthpiece 35 to the connector 25A for joining the cartomizer to the body 20. A reservoir of liquid 360 is provided around the air passage 335. This reservoir 360 may be implemented, for example, by providing cotton or foam soaked in liquid. The cartomizer 30 also includes a heater 365 for heating liquid from reservoir 360 to generate vapor to flow through air passage 355 and out through mouthpiece 35 in response to a user inhaling on the e-cigarette 10. The heater 365 is powered through lines 366 and 367, which are in turn connected to opposing polarities (positive and negative, or vice versa) of the battery 210 of the main body 20 via connector 25A (the details of the wiring between the power lines 366 and 367 and connector 25A are omitted from FIG. 3).

The connector 25A includes an inner electrode 375, which may be silver-plated or made of some other suitable metal or conducting material. When the cartomizer 30 is connected to the body 20, the inner electrode 375 contacts the electrical contact 250 of the body 20 to provide a first electrical path between the cartomizer 30 and the body 20. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring is surrounded by the cartomizer connector 370, which may be silver-plated or made of some other suitable metal or conducting material. When the cartomizer 30 is connected to the body 20, the cartomizer connector 370 contacts the body connector 240 of the body 20 to provide a second electrical path between the cartomizer 30 and the body 20. In other words, the inner electrode 375 and the cartomizer connector 370 serve as positive and negative terminals (or vice versa) for supplying power from the battery 210 in the body 20 to the heater 365 in the cartomizer 30 via supply lines 366 and 367 as appropriate.

The cartomizer connector 370 is provided with two lugs or tabs 380A, 380B, which extend in opposite directions away from the longitudinal axis of the e-cigarette 10. These tabs are used to provide a bayonet fitting in conjunction with the body connector 240 for connecting the cartomizer 30 to the body 20. This bayonet fitting provides a secure and robust connection between the cartomizer 30 and the body 20, so that the cartomizer and body are held in a fixed position relative to one another, with minimal wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the body 20 and the cartomizer 30, such as a snap fit or a screw connection.

Figure 4:
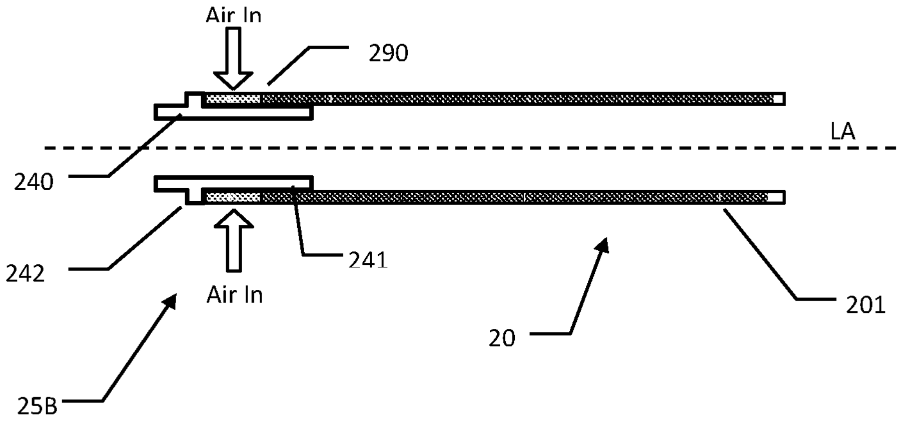
FIG. 4 is a schematic diagram of a body of a delivery device in accordance with embodiments of the description.

FIG. 4 is a schematic diagram of certain details of the connector 25B at the end of the body 20 in accordance with some embodiments of the disclosure (but omitting for clarity most of the internal structure of the connector as shown in FIG. 2, such as trestle 260). In particular, FIG. 4 shows the external housing 201 of the body 20, which generally has the form of a cylindrical tube. This external housing 201 may comprise, for example, an inner tube of metal with an outer covering of paper or similar. The external housing 201 may also comprise the manual activation device 265 (not shown in FIG. 4) so that the manual activation device 265 is easily accessible to the user.

The body connector 240 extends from this external housing 201 of the body 20. The body connector 240 as shown in FIG. 4 comprises two main portions, a shaft portion 241 in the shape of a hollow cylindrical tube, which is sized to fit just inside the external housing 201 of the body 20, and a lip portion 242 which is directed in a radially outward direction, away from the main longitudinal axis (LA) of the e-cigarette. Surrounding the shaft portion 241 of the body connector 240, where the shaft portion does not overlap with the external housing 201, is a collar or sleeve 290, which is again in a shape of a cylindrical tube. The collar 290 is retained between the lip portion 242 of the body connector 240 and the external housing 201 of the body, which together prevent movement of the collar 290 in an axial direction (i.e. parallel to axis LA). However, collar 290 is free to rotate around the shaft portion 241 (and hence also axis LA).

As mentioned above, the cap 225 is provided with an air inlet hole to allow air to flow when a user inhales on the mouthpiece 35. However, in some embodiments the majority of air that enters the device when a user inhales flows through collar 290 and body connector 240 as indicated by the two arrows in FIG. 4.

Figure 5:
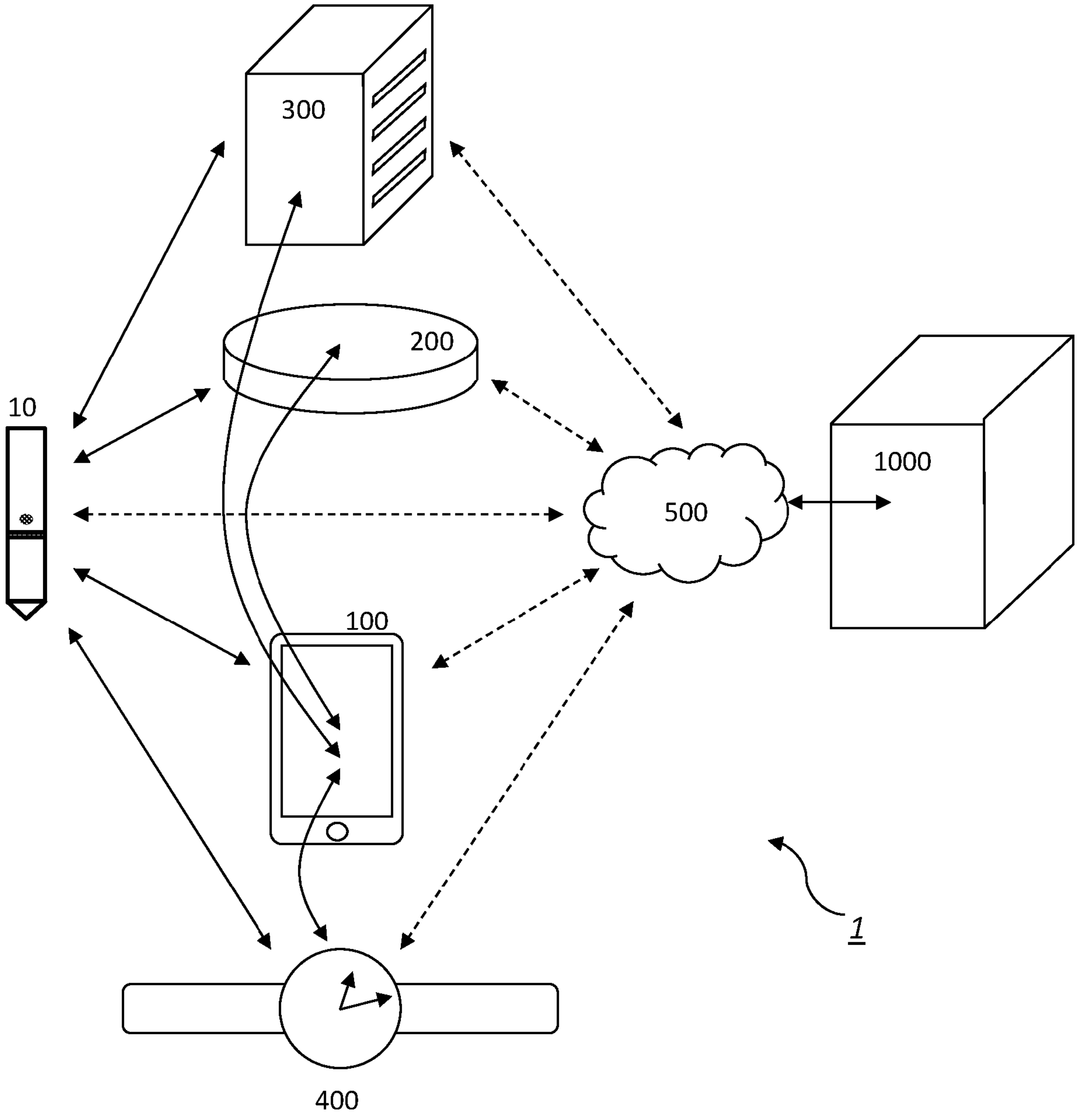
FIG. 5 is a schematic diagram of a delivery ecosystem in accordance with embodiments of the description.

Referring now to FIG. 5, the e-cigarette 10 (or more generally any delivery device as described elsewhere herein) may operate within a wider delivery ecosystem 1. Within the wider delivery ecosystem, a number of devices may communicate with each other, either directly (shown with solid arrows) or indirectly (shown with dashed arrows).

In FIG. 5, as an example delivery device an e-cigarette 10 may communicate directly with one or more other classes of device (for example using Bluetooth® or Wifi Direct®), including but not limited to a smartphone 100, a dock 200 (e.g. a home refill and/or charging station), a vending machine 300, or a wearable 400. As noted above, these devices may cooperate in any suitable configuration to form a delivery system.

Alternatively or in addition the delivery device, such as for example the e-cigarette 10, may communicate indirectly with one or more of these classes of device via a network such as the internet 500, for example using Wifi®, near field communication, a wired link or an integral mobile data scheme. Again, as noted above, in this manner these devices may cooperate in any suitable configuration to form a delivery system.

Alternatively or in addition the delivery device, such as for example the e-cigarette 10, may communicate indirectly with a server 1000 via a network such as the internet 500, either itself for example by using Wifi, or via another device in the delivery ecosystem, for example using Bluetooth® or Wifi Direct® to communicate with a smartphone 100, a dock 200, a vending machine 300, or a wearable 400 that then communicates with the server to either relay the e-cigarette's communications, or report upon its communications with the e-cigarette 10. The smartphone, dock, or other device within the delivery ecosystem, such as a point of sale system/vending machine, may hence optionally act as a hub for one or more delivery devices that only have short range transmission capabilities. Such a hub may thus extend the battery life of a delivery device that does not need to maintain an ongoing WiFi® or mobile data link. It will also be appreciated that different types of data may be transmitted with different levels of priority; for example data relating to the user feedback system (such as user factor data or feedback action data, as discussed herein) may be transmitted with a higher priority than more general usage statistics, or similarly some user factor data relating to more short-term variables (such as current physiological data) may be transmitted with a higher priority than user factor data relating to longer-term variables (such as current weather, or day of the week). A non-limiting example transmission scheme allowing higher and lower priority transmission is LoRaWAN.

Meanwhile, the other classes of device in the ecosystem such as the smartphone, dock, vending machine (or any other point of sale system) and/or wearable may also communicate indirectly with the server 1000 via a network such as the internet 500, either to fulfil an aspect of their own functionality, or on behalf of the delivery system (for example as a relay or co-processing unit). These devices may also communicate with each other, either directly or indirectly.

In an embodiment of the description, to form a user feedback system as will be described later herein, the server 1000, the delivery device, such as for example the e-cigarette 10, and/or any other device within the delivery ecosystem, may utilize one or more sources of information within the delivery ecosystem or accessible by one or more devices within it in order to be more accurately responsive to the user's state. These may include a wearable or mobile phone (or any other source, such as the dock or vending machine), or sources such as a storage system 1012 of the server. The delivery device may also provide information (such as data relating to interaction with an e-cigarette) to one or more data receivers within the ecosystem, which again may comprise one or more of a wearable, mobile phone, dock, or vending machine, or the server.

To form a user feedback system as will be described later herein, a device within the delivery ecosystem, such as the delivery device 10, may utilize one or more processors to analyze or otherwise process this information, in order to estimate the user's state and/or estimate a form of feedback action determined to alter the estimated state of a user (whether a typical/default user, or a user of a similar demographic to the current user, or specifically the current user), for example by causing modification of one or more operations of the delivery device or another device in the delivery ecosystem.

It will be appreciated that the delivery ecosystem may comprise multiple delivery devices (10), for example because the user owns multiple devices (for example so as to easily switch between different active ingredients or flavorings), or because multiple users share the same delivery ecosystem, at least in part (for example cohabiting users may share a charging dock, but have their own phones or wearables). Optionally such devices may similarly communicate directly or indirectly with each other, and/or with devices within the shared delivery ecosystem and/or the server.

It will be appreciated that references to 'the user's state' encompass one of many states of the user, or equivalently one aspect of the overall state of the user. Hence for example the user's level of stress, which as a non-limiting example may be a combination of social circumstance and cortisol levels, is an example of 'the state of the user', but does not completely define the user. In other words, the state of the user is a state relevant to the potential intervention of one or more feedback actions as described elsewhere herein.

User Feedback System

Figure 6:
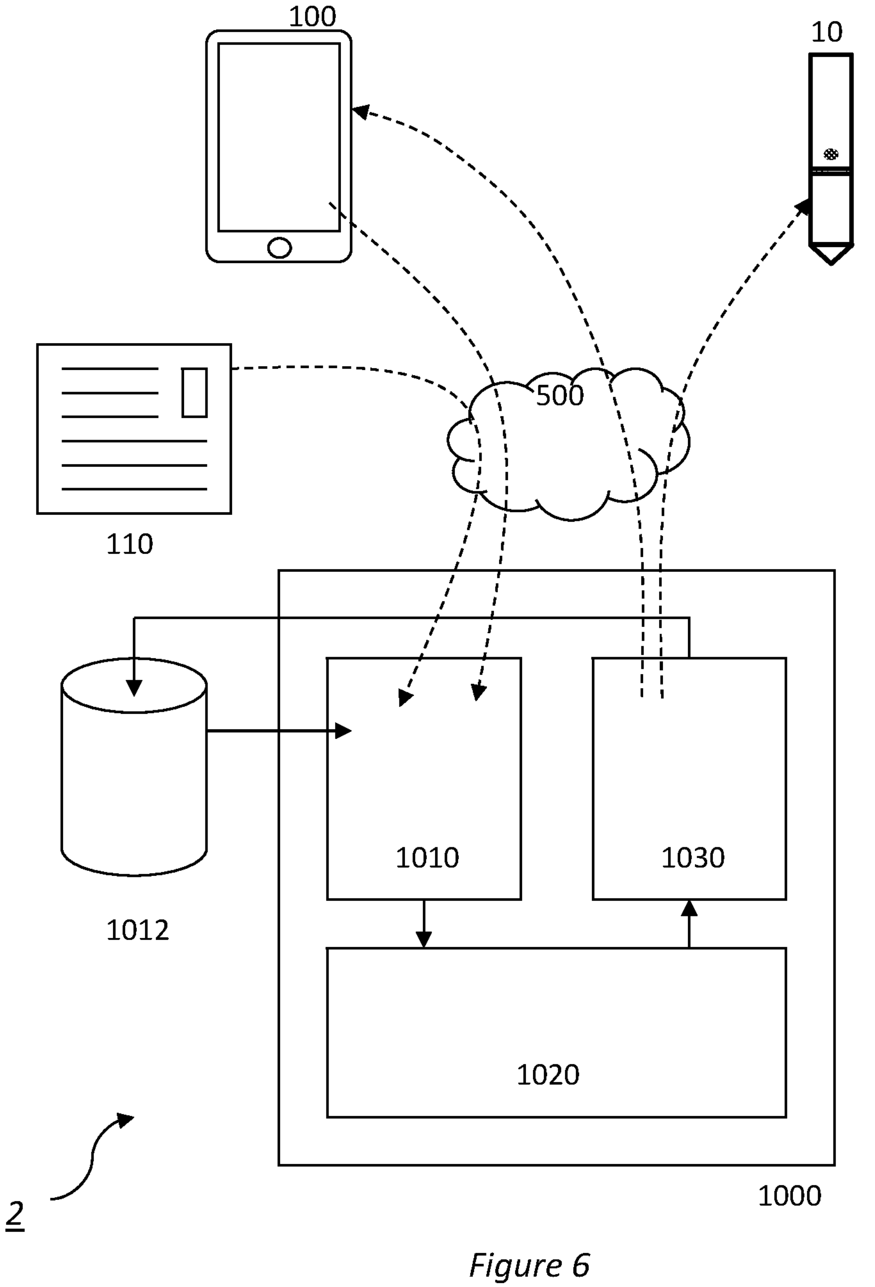
FIG. 6 is a schematic diagram of a user feedback system in accordance with embodiments of the description.

Referring now to FIG. 6, in an embodiment of the description, a user feedback system 2 for a user of a delivery device within a delivery ecosystem 1 comprises an obtaining processor 1010 operable to obtain one or more user factors indicative of user state, an estimation processor 1020 operable to calculate an estimation of user state based upon one or more of the obtained user factors, and a feedback processor 1030 operable to select a feedback action for at least a first device within the delivery ecosystem, responsive to the estimation of user state, in a manner expected to alter the estimated state of a user.

FIG. 6 illustrates one possible embodiment of such a user feedback system as a non-limiting example.

In this embodiment, the obtaining processor 1010, estimation processor 1020, and feedback processor 1030 are located within the server 1000. However, it will be appreciated that any one or more of these processors may be located elsewhere within the ecosystem 1, or its role may be shared between two or more processors in server and/or the ecosystem. For example the obtaining processor may be located in an e-cigarette or mobile phone, or the feedback processor may be located in a vending machine or e-cigarette, or the functionality of these processes may be shared between the server and such devices. In other examples, these processors may be local to the delivery device (e.g. an e-cigarette), or to a delivery system comprising the delivery device and a mobile phone.

Obtaining Processor

The obtaining processor 1010 obtains or receives one or more user factors from one or more sources, with the user factors being in one or more classes of data.

Such user factors may have a causal and/or correlating relationship with the user's state, or some other predictable relationship with it. Whilst such a state may be associated with what is colloquially referred to as the user's 'mood', the user's subjective mood per se is not a primary consideration of the feedback system; rather, the feedback system relates to the correspondence between obtained user factor(s) and user states, and user states and a form of feedback action that may alter such a state of the user, typically in a predetermined manner that is beneficial to the user.

Further it will be appreciated that where there is a correspondence between user factor(s) and states, and states and feedback, there is also in principle a correspondence between the user factor(s) and the feedback, without the intervening state necessarily needing to be explicitly estimated.

The classes of data obtained by or for the obtaining processor include but are not limited to: indirect or historical data; neurological or physiological data; contextual data; environmental or deterministic data; and use-based data.

Indirect or Historical Data

Indirect or historical data provides background information about the user that is not necessarily related to their immediate circumstances (e.g. not their immediate environment or context), but which may nevertheless have an influence on the user's state.

Examples of indirect or historical data include but are not limited to the user's purchase history, previously input user preference data, or behavioral patterns in general. Hence more generally, user choices or actions, typically relating to the delivery device but typically not directly derived from use of the delivery device itself.

Optionally, such information (or indeed any persistent information, such as preferred user settings, or model data for user state and/or feedback action as described elsewhere herein, account details, or other stored user factor data), can be transferred between devices where a given user purchases or uses different delivery devices, so that such information does not need to be re-acquired for new or respective devices. Such information can be transferred or shared for example by direct data transfer via Bluetooth® link between old and new devices. However, since a potential reason for buying a new device is because a previous one has been lost, alternatively or in addition the information may be transferred or shared by (also) holding the information remotely in association with an account/user ID to which different delivery devices/systems of the user are then also associated. Hence a system with learnt/obtained indirect or historical data on an old device may be transferred or shared to a new device either directly between devices or via a centralized user account.

As an example of historical information, purchase history may be indicative of a user's state, being indicative of a general state of the user long term (for example in terms of significant or recurrent purchases), and/or a recent state of the user (for example in terms of recent purchases, or purchases that are likely to still influence the user).

Hence purchase history that may be indicative of the user's state includes type(s) of products bought, frequency of purchase, and the like (not necessarily limited to products directly related to the delivery device or its consumables), how they are bought (e.g., online vs shop), and volume of purchases in a time period. The correspondence between how purchases (and the purchased product or service) affect a user's state can be initially determined on a population basis (e.g. to enable a statistically significant amount of data to be collated), or on a subset of such a population having similar demographics to the user, and/or on the basis of the individual user.

The obtaining processor may obtain indirect or historical data from a number of sources, including user profile data held in storage 1012 at the server, for example comprising previously input user preference data, and/or similarly logs of interactions and/or usage patterns; web or Internet based data 110 such as purchasing records received from vendors or other partners; information gathered with consent by a mobile phone 100 of the user, variously relating to input user preference data, on-line purchases, interaction/usage data (for example where the phone operates in tandem with an e-cigarette or other delivery device as a delivery system local to the user), user questionnaires, and the like. Similarly alternatively or in addition the obtaining processor may obtain such data from the delivery device itself.

Neurological and/or Physiological Data

Neurological and/or physiological data is descriptive of the physical state of the user, in terms of mind and/or body. The data can be descriptive of the user's state on various timescales, including immediate status or changes in state (such as for example heart rate), longer term status or changes in state (such as hormonal cycles), or chronic status, such as fitness levels.

Non-limiting examples of long-term data, for example in the order of multiple months to years, include indicators of the user's metabolism, body shape (e.g. ectomorph, mesomorph, endomorph) or body mass index; chronic disease; any other long term condition such as pregnancy; and activity/fitness level.

Such data may be obtained by or for the obtaining processor from one or more user questionnaires (for example either a questionnaire completed specifically to assist the user feedback system, and/or a questionnaire completed for any third-party partner, for example for a fitness wearable device or social media provider); medical or insurance records by consent; or at least in part from other devices such as a fitness wearable 400 and/or other devices in a wider ecosystem 1 such as smart scales.

Non-limiting examples of medium-to-long-term data, for example in the order of multiple weeks to months, include a user's hormonal levels or hormonal cycles for hormones such as estrogen, testosterone, dopamine and cortisol; any acute condition or illness; and activity/fitness level.

Non-limiting examples of medium term data, for example in the order multiple days to weeks, include a user's sleep cycle; any acute condition or illness; and a user's hormonal levels or hormonal cycles for hormones such as estrogen, testosterone, dopamine and cortisol.

Non-limiting examples of medium to short-term data, for example in the order of multiple hours to days, include the user's degree of wakefulness; their degree of activity; appetite or fullness; blood pressure; temperature; and again any acute condition or illness, and/or hormones.

Again such medium term data (whether longer or shorter) may be obtained by or for the obtaining processor from questionnaires, medical or other records, or fitness or other smart devices. Hence for example hormonal levels may be obtained or inferred from questionnaires, medical or other records, diary or calendar entries with consent, and/or fitness or other smart devices, including for example pinprick blood tests. Similarly blood pressure, temperature, degree of activity and the like can be obtained from smart devices (typically wearables) or user input.

Non-limiting examples of short term data, for example in the order of multiple minutes to hours, include the user's sweat response; galvanic skin response (phasic and/or tonic); their degree of activity; appetite or fullness; blood pressure; breathing rate; temperature; muscle tension; heart rate and/or heart rate variability; and again any acute condition or illness, and/or hormones.

In addition, neurological and/or physiological information specific to the delivery device may also be obtained by the obtaining processor, such as the cumulative amount of vapor generated within the short term (for example within a preceding period corresponding to one, two or more times the pharmacological half-life of the active ingredient in the user's body).

Non-limiting examples of immediate data, for example in the order of seconds to minutes, include the user's body position; blink rate; breathing rate; heart rate; heart rate variability; brain wave pattern; galvanic skin response (e.g. phasic); muscle tension; skin temperature; voice (e.g. qualities such as volume, pitch, breathiness); and their degree of activity.

Again short-term and immediate data may be obtained by or for the obtaining processor typically from biometric sensing, for example using smart devices, or using any suitable approach described herein. For example galvanic skin response could be measured by electrodes on the delivery device; heart rate can be obtained by optical scanning of a blood vessel on the wrist by a wearable device, or by use of an electrocardiogram (ECG) or other dedicated strap-on device. Similarly brainwave patterns can be detected by an electroencephalogram (EEG), and muscle tension can be detected by electromyogram (EMG). Meanwhile body position, blinking and the like can be captured for example by a camera on a phone or in a vending machine.

It may be that short term and immediate physiological data are difficult to obtain; for example a smartwatch may only check the user's heart rate every 10 minutes, meaning that for a given puff the available data is too old to have direct relevance. Similarly a user may wear gloves, making galvanic skin response unavailable. Other data may require the users chose to wear an appropriate sensor, which they may not do consistently. Similarly, some short term and immediate data may indicate values that have multiple causes, and hence may indicate multiple states of the user. For example an elevated heart rate may suggest that the user is stressed, or may indicate that the user is enjoying exercise. Consequently it may be that optionally such short term and immediate physiological data is only used in conjunction with other contextual data that serves to disambiguate the readings. For example, an elevated heart rate during office hours, where the user is located at work and is not travelling a significant distance is much more likely to be a sign of stress than the same hear rate on a Saturday morning when the user is detected as travelling at a running pace near their home.

Hence short term and immediate physiological data (and as appropriate any neurological or physiological data that may require contextual disambiguation) may be discounted, or have a reduced weighting, in the obtaining and packaging of data and/or the evaluation of the user's state, or optionally may be used or more fully weighted when disambiguating contextual data is also obtained that indicates the type of state that the data is likely to relate to.

To the extent that the same examples span different time frames in the above description, it will be appreciated for example that different hormones, hormonal cycles, fitness levels and the like can have shorter and longer term characteristics. It will also be appreciated that where an example of data is included in one list but not another, this does not preclude the data being gathered/used over a different time frame; for example blood pressure may be listed as an example of short term data, but clearly may also be part of longer term data, for example due to ongoing high blood pressure.

As with indirect or historical data, data of a plurality of these types and/or from multiple sources may be used in any suitable combination.

In addition to directly measured neurological or physiological data, any suitable analysis or data fusion may be implemented to obtain data of particular relevance to the delivery device regarding the user's state.

For example, the feedback system may be operable to estimate a current nicotine concentration (as a non-limiting example of an active ingredient), or a concentration of active or inactive compounds that break down from the consumed ingredient, within a user (and subsequently deliver nicotine/the active ingredient accordingly).

Hence in principle the feedback system (for example in a pre-processor or subsystem of the obtaining processor) may estimate the concentration of nicotine in the user based on monitoring the nicotine consumed, the time at which it is consumed, and having stored the value for the half-life of nicotine in the body (around 2 hours, although this value can be refined based on information regarding the individual, such as height, weight etc.). Such monitoring can be performed based on usage data from the delivery device. Hence for example based on the original active ingredient concentration, and a predetermined relationship between heating/aerosol generator power and aerosol mass output, an mass of active ingredient per unit volume inhaled may be estimated; from that, using predetermined absorption relationships (optionally based on analysis of depth/duration of inhalation, using airflow data), the amount of active absorbed may be determined; finally the body mass of the user, and potentially other factors such as a age, gender and the like may be used to determine the concentration of active ingredient and/or breakdown products in the user over time. Again, here nicotine is a non-limiting example of an active ingredient.

It has been found that users typically try to have a nicotine level which is between an upper and lower threshold (which may be different between users), which collectively may be regarded as defining a 'baseline' level. The feedback system can establish such a baseline (e.g., by monitoring use over time), and, as will be described in more detail later herein, the feedback system can select and optionally cause modification of one or more operations of the delivery device to deliver nicotine to match the baseline. The baseline may be a steady value or may vary, e.g. with time of day or day of week. It may be initially estimated based on a profile of the user obtained for example from a questionnaire, and/or built up or refined by information (measured and/or self-reported) from the user.

Such a modification may be expected to alter the estimated state of a user, in a positive manner, as it has been previously determined that the chance that a user will be in a positive mood increases when their nicotine levels are close to their personal baseline or thresholded range.

Where a user consumes several different active ingredients, each may have its own baseline thresholds. Optionally, the feedback system can monitor whether consumption of one active ingredient overlaps another to the extent that one active ingredient may affect the baseline of another, and if so modify these accordingly, for example based on stored pharmokinetic data relating to such overlaps.

As noted previously, in these circumstances it is likely that the user interacts with multiple delivery devices to consume the different active ingredients, and the usage from each device may be combined for the associated user. Alternatively, where a single device can switch between payloads (for example hating different gels), or has a mixed payload of actives, the currently heated payload or payload mix can be communicated to the feedback system for the purposes of tracking consumption.

Contextual Data

Contextual data relates to situational factors other than environmental factors (see elsewhere herein) that may affect the user's state. Typically such situational factors affect the user's psychological state or disposition towards stress, calm, happiness, sadness, or certain patterns of behavior, and hence may also influence and/or have a correlation with neurological and physiological user factors such as dopamine, adrenaline, or cortisone levels, blood pressure, heart rate and the like as described elsewhere herein.

Examples of contextual data include the user's culture, including at a broad scale where they live, their religion if they have one, and at a narrower scale their job and/or employment status, educational attainment and the like, and social economic factors that may interact with these such as gender and relationship status.

Such information may be obtained by or for the obtaining processor from user questionnaires, social media data, and the like.

Other contexts include the season (e.g. winter, spring, summer, autumn) or month, and any particular events or periods within that season or month, such as Lent, Easter, Ramadan, Christmas and the like. For example, users are more likely to see consumption at or below their personal baseline as a positive thing during Lent, or the first few weeks of January.

Such information may be obtained by or for the obtaining processor from a calendar and database of events, suitably filtered if appropriate according to other contexts such as country, religion, employment, gender and the like as described previously.

Other contexts include the user's agenda or calendar, which can indicate sources of stress or relaxation, and how busy or otherwise the user is at a given time. Hence for example a social event may be associated with a positive influence on user state, for example raising dopamine levels, whereas a medical appointment or driving test may be associated with stressors such as an increase in cortisol and heart rate. Similarly events, appointments, and/or reminders in rapid succession may indicate a negative effect on the user's state.

The user's agenda or calendar can also provide an indication of the user's likely location, which may affect either their state, or their ability to use the delivery device in a manner that may modify that state. For example, the user may have different typical states, and different abilities to use their delivery device, depending on whether they are at home, at work, in outdoor or indoor public spaces, in an urban or countryside environment, or commuting. The relationship between user state and location may at least initially be based on data from a corpus of users. Alternatively or in addition this relationship may be built up or refined based on data from the user (e.g. measured or self-reported). It will be appreciated that the user's location may also be determined from a GPS signal obtained by the delivery device or an associated device such as a smartphone, or the registered location of a vending machine or point of sale unit.

With regards to commuting or other modes of travel, the type of travel may influence the user's state. For example, walking may have a more positive effect on the user's state than driving, for example in terms of heart rate, blood pressure and the like. It will be appreciated that this context illustrates the potential for the combination of contexts to be significant, as walking in the sun versus walking in the rain may have different effects on the user's state. The type of travel may for example be inferred from GPS data from the user's phone, or the pairing of the phone or delivery device with a vehicle, or the purchase of public transport tickets, or a questionnaire indicating travel habits/times.

Such information may be obtained by or for the obtaining processor from work or personal digital calendars, for example on the user's phone. It will also be appreciated that the user's phone, or other smart wearable, may directly provide an indication of the user's location, and/or historical patterns of location, for example corresponding to a user's home and work locations and average commuting times.

Other contexts include the weather in the user's location or the upcoming weather in the user's location or upcoming location. Depending on the user, sunny weather is likely to improve the user's mood and sociability, whilst poor weather is likely to lower the user's mood and potentially reduce their sociability or affect their ability to socialize. For example, some users are likely to behave so as to consume active ingredients to an extent that reflects their expectations of mood as suggested by the weather, optionally in conjunction with other contextual factors and further user factors as described herein.

Such information may be obtained by or for the obtaining processor from a weather app, which may be located on a smart phone 100 of the user, or accessed directly for example by the server 1000. More generally weather data may be obtained in response to GPS data (for example by the smartphone), and/or using a local weather measuring system such as a barometer.

Other contexts include the user's proximity to other people, either generally in terms of crowds or social setting, or specifically in terms of other individuals with which there is in principle a measurable correlation with user behavior. For example, a user may have a different state depending on whether they are in proximity to their boss, their work colleagues, the friends, their partner, their children, or their parents. Hence for example the user may have a different state in a crowded or sociable environment versus when alone or with a partner or family members.

Such proximity can be inferred from the user's agenda or calendar, their mobile phone, their delivery device, or their location. The user may self-report their social status either specifically for the purpose of the user feedback system herein, or generally for example on social media; meanwhile a phone and/or delivery device for example may detect signals from other phones and/or delivery devices for more than a predetermined period of time, indicating they are remaining in each other's presence. Optionally a phone's camera may be used to detect others, but this may not be available if the phone is in a pocket or bag. The feedback system can also determine the proximity of users of the delivery device with other users of such a delivery device—e.g. any suitable delivery device whose location can be determined by the feedback system (for example directly or via an associated mobile phone), whether or not that other delivery device is part of a feedback system itself. Similarly the feedback system can determine the proximity of specific people whom the user has, with permission, identified to the feedback system; for example by providing their phone number to the feedback system, or the system associating a detected Bluetooth® or other ID with that user.

A user may also indicate (for example via a questionnaire) their typical state in response to different social situations, groups or individuals, whether at a broad level such as 'introverted' or 'extroverted', or more specifically.

It will be appreciated that other contexts exist that may influence the user's state, such as recently consumed information; social media content, news articles, streamed video, e-books, e-magazines, photos and other similar content that may be obtained by or for the obtaining processor. Some content may be assumed to have a universally consistent effect on the state of users, such as for example news of a natural disaster, whilst other content may affect individuals differently, such as the results for a user's preferred sports team, and be assessed individually, for example based upon results of a user questionnaire.

The content of the consumed information may be assessed, for example for keywords, to generate a rating for positive or negative influence on the user's state. Optionally only the rating may be obtained by or for the obtaining processor, or any suitable digest, such as a keyword selection. More generally the obtaining processor may only receive a digest of user factors as appropriate, particularly where the source material does not itself enumerate some user factor property.

Likewise, usage of devices other than the delivery device may influence the user's state. In particular a choice of apps on the user's phone, and the interaction, type of interaction, and/or duration of interaction with them may have correlations with the user's state; for example social media or playing a gaming app may raise dopamine and/or cortisol levels, heart rate, and the like; whilst listening to a music app may reduce heart rate and/or cortisol levels. The duration of interaction may have a linear or non-linear relationship with these changes of state, or may with time indicate a different state; for example playing a game for a long time may indicate boredom.

It will be appreciated that for many user factors, not merely contextual but of other types as well, a situational response (e.g. an expected state) may at least be initially based upon data from a cohort of users (for example a prior test population of users), but alternatively or in addition may be built up or refined from information obtained from the user (whether measured, received or self-reported).

Environmental and Deterministic Data

Environmental and deterministic data effectively relate to long-term context data outside of the user's choice or influence. There is some overlap with longer term contextual influences such as culture; hence for example the user's upbringing, their genetics, gender, biome internally (for example they gut biome) and/or externally (for example whether they live in an arid or verdant environment), and age.

As with other data described herein, such environmental and deterministic data may be obtained by or for the obtaining processor from one or more user questionnaires (for example either a questionnaire completed specifically to assist the user feedback system, and/or a questionnaire completed for any third-party partner, for example for a fitness wearable device or social media provider). Amongst other things, such a questionnaire may ask for details such as sex/gender, height, weight, ethnicity, age, etc. Such a questionnaire may also comprise psychometric test questions to estimate a user's mental predisposition and/or history (e.g. one or more of extrovert/introvert, active/passive, optimist/pessimist, calm/anxious, independent/dependent, content/depressed, and the like). Such a questionnaire may also ask questions related to the user's culture and beliefs (e.g. one or more of: a country of own or parent's origin; religion, if any; political persuasion, if any; newspapers or news websites read, if any; other media consumption, if any; and the like). Again as with other data described herein, some such environmental and deterministic data may be obtained by or for the obtaining processor from medical or insurance records by consent; and/or may be inferred from the user's location, as appropriate.

Not all environmental and deterministic data need be long-term; hence for example the time of day, day of the week and month of the year may be considered environmental and deterministic data. Hence for example the user state may vary over the course of a day or week, for example being different during weekdays and weekends, and/or during work hours of the weekday versus evenings, and also potentially at specific times of day. Similarly there may also be overlap for example with other contextual data, such as the weather. Again there may also be synergy between different user factors; for example the time of year may affect the amount of daylight (in terms of both the length and potentially also weather patterns). The level and/or duration of daylight, either as measured (e.g. using a light sensor/camera on a device within the delivery ecosystem) or as inferred from the date, may also have a detectable relationship with the user's state. The quality of light (e.g. color temperature, indoor/flickering or outdoor, day or night, seasonal mean levels, etc.) may also be treated as a user factor.

Use-Based Data

Use-based data relates to direct interactions of the user with the delivery device and/or optionally any other device within the delivery ecosystem or which can report on interactions with it to the feedback system (e.g. to the obtaining processor). These interactions may relate to vaping/consumption and/or manipulation/handling and/or setting the device.

Vaping/consumption based interactions may relate to inter-inhalation properties such as the number, frequency, and/or distribution/pattern of puffs/acts of consumption within one or more chosen periods. Such periods may include daily, hourly, as a function of location, as a function of pharmokinesis (for example the active ingredient half-life within the body for one or more delivered active ingredients), or any other period that may be relevant to the user's state, and/or chosen to increase the apparent correlation between number, frequency and/or distribution/pattern of puff/consumption and a user's state; for example the period may be equal to the average period of time taken to smoke a conventional cigarette, either for the individual user or as a general population average.

Vaping based interactions may also relate to intra-inhalation properties such as individual vaping actions or statistical descriptions of a cohort thereof (for example but not limited to a cohort within one of the above-described chosen periods), such as duration, volume, average airflow, airflow profile, active ingredient ratio, active ingredient delivery timing, heater temperature, and the like.

Data relating to vapes and vaping behavior (or more generally consumption) as described above may be obtained by or for the obtaining processor from a delivery device itself, for example via a Wi-Fi® connection to the server 1000, or via communication with a companion mobile phone 100 or other local computing device, paired to the delivery device 10 for example via a Bluetooth® connection to form a delivery system. However, in principle at least some data relating to consumption may be obtained from one or more other devices within the delivery ecosystem; for example an associated mobile phone may log vaping events to collate frequency/distribution data. Similarly, a wearable sensor may determine the degree of volume of inhalation based on just movement. Hence one or more sensors relating to the determination of vaping based interactions may be located externally to the delivery device, although typically least one will be internal to the vaping device, the most frequent being an airflow sensor that is typically used to detect the onset of inhalation and activate the aerosolization mechanism of the device (in turn, typically a heater as discussed previously herein). In any event, such internal or external sensors either singly or in combination represent examples of a sensor platform.

In any event, consequently the user feedback system comprises at least a first sensor platform (internal and/or external to the delivery device 10) comprising at least a first sensor operable to detect at least a first physical property associated with at least a first user inhalation action.

As noted previously, the or each physical property can be one or more of an intra-inhalation property or an inter-inhalation property.

The delivery device may comprise one or more airflow sensors as described previously herein to determine when the user vapes and/or how the user vapes, for example as characterized above, and raw data relating to vaping/consumption events may be stored in the memory of the delivery device or transmitted to the companion mobile phone or any other suitable device within the delivery ecosystem. The data may then be used to determine features such as the number, frequency, and/or distribution/pattern of puffs/acts of consumption within one or more chosen periods, and/or the duration, volume, average airflow, airflow profile, average ingredient ratio, and/or heater temperature values for one or more vaping/consumption events, using a processor of the delivery device and/or the any other device within the delivery ecosystem.

Optionally at least one sensor of a sensor platform may be adapted to sense at least two of puff profile, puff frequency, puff duration, number of puffs, session length, peak puff pressure and determine the state/mood of the user from the sensed information.

A user's puffing behavior provides a useful indicator of stress vs non-stressed states. In particular, the intensity and frequency of a user's puff has been found to change from a normal level during instances of stress (e.g. to stronger and shorter puffs, and more frequent puffs). Therefore optionally the delivery device or another device within the delivery ecosystem (such as the user's mobile phone) or a back end server may establish baseline profiles, frequencies, patterns, puff numbers, peak pressures and the like as described elsewhere herein, and subsequently detect deviations from this baseline (e.g. above a predetermined threshold) indicative of stress. Further optionally different baselines may be set for different situations and contexts, such as time of day, day of week, and location; for example a user might be more stressed at work than at home, but this partial elevation of stress may be considered a baseline for a work context, and only further stress might be considered to be a deviation that indicates a change of user stress that may prompt a response.

In any event as noted above, such information may then be packaged and sent to the obtaining processor as one or more user factors.

Manipulation/handling based interactions may relate to how the user interacts with the delivery device when not actively vaping on it; for example to characterize whether the delivery device is kept in a bag until immediately prior to use, or whether the user plays or fidgets with the delivery device in between uses.

Hence for example the delivery device or any other handheld device within the delivery ecosystem, such as the user's mobile phone may comprise a sensor for detecting handshake; that is to say, small involuntary movements (so-called micro-movements) of the user's hand, such as trembling. Such micro-movements may be indicative of a state of the user. For example the amount, frequency, or prevalence of such micro-movements, and/or the amplitude of such micro-movements, are likely to have a correlation or correspondence with one or more of user stress, adrenaline, autonomic nervous system function, user fatigue, user focus, and a user's deviation from a preferred baseline amount of active ingredient within their body.

In particular, micro-movements or tremors in the range 1-15 Hertz, or more preferably 2-11 Hz or still more preferably 3 to 9 Hz are considered indicative of elevated stress or arousal, and so detection of such motion may be used as an input indicative of stress. Conversely, optionally manipulations that are e.g. lower frequency may be considered indicative of lower stress. Similarly movements that are not 'micro' movements (i.e. deliberately swinging the device, as opposed to holding it in a trembling hand) may either be ignored for the above purposes, or analyzed for other significance (e.g. a motion characteristic of imminent use, or associated with a wider context for which a user state has a clear correlation).

Hence in some implementations, a user feedback system for a user of a delivery device within a delivery ecosystem may include: an obtaining processor adapted to obtain one or more user factors indicative of a state of the user, the one or more factors including the output from a motion sensor configured to detect micromovements or tremors of a user;

an estimation processor adapted to calculate an estimation of user state based upon one or more of the obtained user factors including at least the output from the motion sensor; and a feedback processor adapted to select a feedback action for at least a first device within the delivery ecosystem, responsive to the estimation of user state, expected to alter the estimated state of a user. In some implementations, the obtaining processor obtains only the output of the motion sensor as the one or more user factors, and the estimation processor calculates an estimation of the user's state based only on the output of the motion sensor. In some implementations, the motion sensor is provided in or on an aerosol provision device of the delivery ecosystem. In some implementations, the feedback action includes altering the operation of an aerosol provision device.

Also for example, separate to micro-motions, a given user tends to hold their delivery device more often and/or for longer in times of stress than when relaxed or in a calm scenario. This may be because the user has made a conscious or unconscious link between the device and a reduction in stress caused by vaping with it. Such holding may be detected using one or more accelerometers and/or touch sensors as mentioned elsewhere herein.

Optionally the delivery device or another device within the delivery ecosystem (such as the user's mobile phone) or a back end server may establish baseline levels of holding and/or physical interaction with the delivery device for the purpose of detecting when increased holding and/or physical interaction occur (e.g. above a predetermined threshold), and similarly optionally may correlate such normal or elevated levels with other indicators or correlates of the user's state and/or with the user's state directly so that holding and/or physical interaction can provide a (further) indication of user state and/or act as a proxy for another source of such indications if this is normally used/preferred but currently unavailable. As with puffing behavior, Further optionally different baselines may be set for different situations and contexts, such as time of day, day of week, and location; for example a user might be more stressed at work than at home, but this partial elevation of stress may be considered a baseline for a work context, and only further stress might be considered to be a deviation that indicates a change of user stress that may prompt a response.

Hence in some implementations, a user feedback system for a user of a delivery device within a delivery ecosystem includes: an obtaining processor adapted to obtain one or more user factors indicative of a state of the user, the one or more factors including the output from one or more sensors configured to detect when and/or how a user is holding a device of the delivery ecosystem; an estimation processor adapted to calculate an estimation of user state based upon one or more of the obtained user factors including at least the output from the one or more sensors; and a feedback processor adapted to select a feedback action for at least a first device within the delivery ecosystem, responsive to the estimation of user state, expected to alter the estimated state of a user. In some implementations, the In some implementations, the obtaining processor obtains only the output of the one or more sensor as the one or more user factors, and the estimation processor calculates an estimation of the user's state based only on the output of the one or more sensors. In some implementations, the one or more sensors are provided in or on an aerosol provision device of the delivery ecosystem. In some implementations, the feedback action includes altering the operation of an aerosol provision device.

More generally in some implementations, for a user feedback system the one or more user factors include one or more user factors selected from the group comprising: one or more user inhalation characteristics, output from one or more motion sensors configured to detect micromovements or tremors of a user, and the output from one or more sensors configured to detect when and/or how a user is holding a device of the delivery ecosystem; the inventors appreciate that a strong correlation exists between the data obtained from these user factors and the determination of a user being in a stressed state.

The delivery device may comprise one or more touch by sensors or accelerometers to determine such interactions. Similarly, the device may comprise buttons and other settings for which user interactions may be logged. Interactions with buttons and other settings relating to the delivery device on a companion mobile phone may also be logged. Such interaction data may then be packaged and sent to the obtaining processor is one or more user factors.

It will be appreciated that detecting touch may be one of several functions of a sensor in a sensor platform; for example physiological data may also be obtained using such sensors, or conversely such physiological sensors may also provide a touch detection function. Hence a galvanic skin response detector and/or heart rate detector may detect a touch and other physiological properties of the user at the same time. Such a sensor may be located on a grip part of the delivery device, for example where one or more of the user's fingers and/or where the user's palm are likely to hold the device for a prolonged period of time (for example when compared to contact with the mouthpiece of the delivery device or any buttons or other user interface elements of the delivery device).

Galvanic skin response detectors typically work by measuring skin conductivity or electrodermal activity, which in turn is typically a function of user perspiration (often in minute amounts, and typically do this by applying a low constant voltage to the user's skin (for example through a grip part of the delivery device) and then measuring how skin conductance (resistance) varies. Typically there is a tonic or slow fluctuating component in the order of seconds to minutes, and a faster varying phasic component fluctuating within seconds. Either component may be indicative of the user's state and may hence be a physical property contributing to user factors for the user feedback system. Notably both positive and negative stimuli (for example joy or stress) can increase galvanic skin response; hence optionally other contextual information may be useful to disambiguate the signal. However, separately there is also a clear correlation or correspondence between galvanic skin response and the consumption of certain active ingredients such as for example nicotine.

Meanwhile heart rate detectors of the type most frequently found in wearables and which may for example be found in the delivery ecosystem, for example in a wearable or in a mobile phone or delivery device typically comprise an LED light source and sensor; the sensor detects reflections from the light source after it has passed through the user's skin and been reflected back at least in part by blood as it pulses through veins and arteries; the pulsing action results in a characteristic variance in the amount of light reflected, and this can be detected to determine the user's heart rate. It will also be appreciated that similar heart rate detectors based on electrodes are available (electrocardiogram or ECG sensors), which detect the electrical activity of the heart, or variations in electrical properties associated with blood pulses.

As noted elsewhere herein, the user's heart rate (whether instantaneous or averaged over a predetermined period of time) may be indicative of their state, and hence may be a physical property contributing to user factors of the user feedback system. Similarly, variability of the user's heart rate may be indicative of the user state, with high variability being associated with stress. It will be appreciated that a heart rate monitor (for example EKG or optical) can in principle generate instantaneous, average, and/or variability-based data using the same sensors. Data from such a heart rate sensor may also be used to detect autonomic nervous System activity (e.g. sympathetic or parasympathetic activity such as fight or flight/rest and digest).

Other sensors associated with physiological measurements may be similarly optionally included within the delivery device or any other device of the delivery ecosystem that the user is likely to interact with in a manner enabling such measurements. These include for example a muscle tension sensor, and/or a cortisol sensor.

Muscle tension can be detected using an electromyogram (EMG), which again may use surface electrodes; typically the EMG data is based on a voltage difference between a recording site and a reference site, where the reference site typically is a bony low muscle point in the body. For a handheld device such as the delivery device, therefore an appropriate site for the reference electrode may be coincident with the fold of a finger or thumb joint; such a position can be predicted based on the molding of the device (for example a grip portion) and the location of activation buttons or any other user interface elements. Muscle tension can also in principle be detected visually (for example in face/neck tension), hence may be detected by a camera of a device in the delivery ecosystem such as the user's phone, or a kiosk/vending machine.

Meanwhile cortisol can be detected using a sensor known in the art and positioned on the mouthpiece of the delivery device; cortisol can be measured in saliva, and so this may be measured from the lips of the user during an inhalation action. Cortisol is also present in sweat, and so in principle could alternatively or in addition be detected using a sensor incorporated into the body of the delivery device where it is held by the user. As noted elsewhere herein, there is a correlation between cortisol and stress levels in a user.

It will be appreciated that electrodes built into the delivery device, for example in the grip region (or any other device in the delivery ecosystem, as described elsewhere herein) may be used for two or more modes of detection such as galvanic skin conductance, heart rate, muscle tension or the like, either in parallel by respective analyses of the same raw signal data, or in a sequential cycle.

Such sensors typically require two electrodes to measure skin conductivity between them. On a relatively small delivery device, optionally the electrodes may be concentric (for example an outer circle and inner circle or disc/point) in order to provide a compact sensor that may be used for example with a fingertip.

The delivery device itself, and/or in combination with any other suitable device of the delivery ecosystem, may optionally comprise one or more of the above sensors in any combination.

Interaction with buttons or other user interface elements may also provide information relating to a state of the user during use of the delivery device. For example, in a delivery device where activation uses a button press or other UI interface, the delivery device may measure the time between such activation and inhalation occurring. This period of time is likely to have a correlation or correspondence with one or more of user stress, user fatigue, user focus, and a user's deviation from a preferred baseline amount of active ingredient within their body. Hence for example the period of time is likely to be shorter if the user is stressed that if the user is calm.

Similarly, the degree of force applied to a button or element of the user interface may be measured, for example in terms of peak force/pressure applied, and/or a force profile, may be indicative of a state of the user. Hence for example a high degree of force (for example above a predetermined threshold) and/or a short interaction with the button or other user interface element may be indicative of user stress, and hence there may be a correlation or correspondence between the degree of force or the shortness of activation and a degree of stress of the user.

As noted above, the delivery device may comprise one or more accelerometers, and/or similarly gyroscopes or other motion sensors (e.g. 3 or 6 axis accelerometers or gyroscopes, and/or a multi-axis compass), through which motion of the delivery device may be determined. Using telemetry from one or more such motion sensors within the delivery device, the user feedback system can detect for example incidental or subconscious manipulation of the device; for example changes in orientation or rotation whilst overall position remains within a predetermined radius and/or moves slowly or generally in a horizontal direction; such motions are indicative of the user toying with the device within their hand whilst either stationary or walking. Such toying may be indicative of a state of the user; for example it may be indicative of at least a subconscious wish to use the device, or to use the device more than is currently the case, and hence correlate with heightened stress, a lack of focus, and/or a user's deviation from a preferred baseline amount of active ingredient within their body.

Similarly such telemetry can be used to detect characteristic gestures associated with use before, during, and/or after a puff, such as lifting the device up and into an engagement position with the user's mouth, and any subsequent disengagement motion. The speed and/or acceleration of these actions may similarly correlate or have a correspondence with the user's mood, for example with more rapid movements or a more direct path from a holding position to the user's mouth being associated with increased stress, and slow or more meandering movements being associated with the user being calm. Similarly positional information such as the angle of the tilt relative to the mouth, or the angle of the tilt relative to gravity, during a puff, may give an indication of user state.

Movement or motion as described above may thus relate to position, velocity, acceleration, orientation and/or rotation, as appropriate to the particular action of the user.

Likewise such telemetry can be used to detect characteristic gestures not associated with use, such as gesticulation by the user, or gross movements of the user for example when climbing the stairs or using a lift, or travelling at speeds and/or in speed profiles consistent with cycling, driving by car, travelling by bus, train or plane; these activities in turn may indicate the state of the user, either in terms of their internal state with regards to breathlessness or exhaustion (in relation to gross movement), agitation or stress (in relation to gesticulation), or in terms of their external state with regards to how easily they can use a delivery device, for example when cycling or on public transport. General activity measurements can also be indicative of user state for example based on a correlation between an active lifestyle and wellness, or that an active day tends to increase dopamine levels and to improve a user's mood the next day. Meanwhile activity may also be interpreted in light of other user factors (for example by the estimation processor), so that activity on a rest day may be indicative of calm, whilst on a busy day or in association with other indicators of stress may indicate restlessness.

Such telemetry can likewise be used to detect other motion, such as a small pendulum action associated with being in a bag, or a larger pendulum action associated with being held in the user's hand as they walk, or a pattern of motion consistent with being in a user's pocket.

In addition to physical manipulation, other interactions with the delivery device or with devices within the delivery ecosystem may optionally be similarly evaluated. For example a microphone in the delivery device or the user's mobile phone may be used to detect the user's voice (for example when speaking specifically to the device, or to other people nearby, or on a phone call, or optionally as an ongoing background activity in a manner similar to a voice activated personal digital assistant). Properties of the user's voice such as volume, word speed, timbre, tonality, pitch, and/or non-harmonic content may be analyzed to determine whether the user is vocalizing in a calm or a stressed manner, optionally after calibration for example to the user's neutral voice. Similarly optionally such a device in the delivery ecosystem may monitor for keywords indicative of different states of the user, whether positive and/or negative.

In a similar manner to vocal expression, alternatively or in addition optionally facial expression may be monitored. In this case, the delivery device or devices within the delivery ecosystem such as the user's mobile phone, or a vending machine, may comprise a camera. In the case of the delivery device, it may comprise one or more cameras positioned to have the user's face within its field of view during inhalation and/or during the action of lifting the device to the user's face (for example on a similar side to the mouthpiece); alternatively or in addition there may be a camera facing away from the user during inhalation, in order to capture details of the user's environment.

Data from images from such cameras can be obtained pertaining to the user's state, including for example the user's overall facial expression, which typically has a strong correlation with the user's subjective mood, but also for example muscle tension in the face as noted previously herein, which tends to correlate with stress, strain, or pain. Meanwhile eye movements can indicate a user's degree of focus and/or the nature of some activities the user is undertaking (for example patterns of eye movement and/or blinking will be different when driving, reading, or socializing, and tend to differ when a person is alert or drowsy). Similarly, if capable of being resolved by the camera, micro-movements in the face or neck can be indicative of heart rate. In principle data from a camera may similarly be used to estimate blood oxygen levels, heart rate, micro expressions, eye movement, and/or eye dilation and the like, as potential user factors.

Such a camera may also be used to obtain other data, such as for example motion based on the relative movement of a scene relative to the camera or key points therein, the detection of people significant to the user, such as a partner or children, the extent or nature of a social situation, such as the number of people in proximity to the user. Similarly such a camera may be used to determine whether the user is indoors or outdoors, based for example on the detection of sky, color temperature, light flickering, characteristic indoor features such as windows or TV screens, or the like.

It will also be appreciated that user interaction may comprise a specific indication of user state by the user. In this case, a user interface is provided that allows the user to select a setting that is an indicator of their state. This indicator may be explicit, for example providing a selection of user states and optionally values (for example from 1 to 100 indicating the degree of a state, so that the user can directly input their subjective assessment of their own state. As noted elsewhere herein, this may be useful for the evaluation processor, and/or for evaluation model training purposes or the construction of rules or look up tables for associating user factors with user states. Alternatively the user interface may be more indirect, for example having a 'calm' mode and 'boost' mode, where the mode is a default for when the user is calm, whereas the 'boost' mode delivers more of the active ingredient per volume of aerosol inhaled and hence may have a correlation with user stress.

In a similar manner to the indications provided by use of a calm mode and boost mode, the selection of a particular consumable (for example one with a normal or calm concentration of active ingredient or one with a high or boosted concentration of active ingredient) may be indicative of the user's degree of stress or calm, typically the start of the day when such consumables are being selected; hence this may be indicative of more chronic levels of stress.

It will be appreciated that where a user has multiple delivery devices 10, usage may be aggregated across these devices, either by obtaining user factor data from each device, or already aggregated via an intermediary such as a phone app or one of the delivery devices acting as a hub for this purpose. Where different devices deliver different active ingredients (whether type or concentration), this may also be accounted for in modelling use, as a non-limiting example in relation to pharmokinesis.

Multiple Data Sources

As noted above, and as shown in FIG. 6, the obtaining processor may receive multiple user factors of the types described herein from one or more sources, such as those in the delivery ecosystem 1, the Internet 110, and records held by the feedback system 1012, for example at the server 1000.

As noted above, these user factors may variously be classified as indirect or historical data; neurological or physiological data; contextual data; environmental or deterministic data; and/or use-based data.

In the case of use-based data, it will be appreciated that multiple sensors, and/or a sensor with multiple sensing capabilities may be used in a sensor platform to obtain some or all of such use-based data.

Whilst the above description recites the sensor platform in relation to serving the feedback system, it will be appreciated that a delivery device such as an aerosol provision device may comprise a such sensor platform anyway, independently of any feedback system, for example to provide information to the user or some other device. Hence any suitable aerosol provision device may have a sensor platform comprising one or more selected from the list consisting of a galvanic skin response detector, a heart rate detector, a touch detector, and any other suitable detector described herein (for example, a cortisol detector); and the or each detector may be located on one or more selected from the list consisting of a grip portion of the delivery device, a mouthpiece of the delivery device and an activation button of the delivery device, as appropriate.

A further location for a sensor platform for one or more sensors is on an optional collar attachment arranged for example to fit between the cartomizer and the main body of the delivery device, or between the main body of the device and a mouthpiece, or between any two user-separable components of the delivery device, as appropriate. The collar may be user-attachable, may be user-detachable, or may be integral to the device. The collar may for example thus encircle and form part of the airflow path within the delivery device, and comprise the (or a further) airflow sensor, for example to detect puff strength or profile, or comprise one or more accelerometers or gyroscopes to detect one or more of device orientation, acceleration, velocity, or position, or any other suitable sensors (e.g. a touch sensor). The collar can draw power from the delivery device for example whilst passing power on to the cartomizer. The collar may also include a Bluetooth® link and antenna (for example an annular antenna). The collar may thus enable retrofitting of capabilities relevant to the techniques herein to a delivery device that may otherwise be unsuitable, or only provide more limited information.

Obtaining Processor Operation

Turning again to FIG. 6, the obtaining processor 1010 is typically part of a remote server 1000, and may receive user factors from diverse sources such as the server's own storage/database 1012, on-line sources 110, and devices within the user's delivery ecosystem 1, such as the delivery device 10 itself, a mobile phone 100, a fitness wearable 400, a docking unit 200, a vending machine 300, and any other suitable device that may provide information relevant to the user's state, such as a voice-activated home assistant, smart thermostat, smart doorbell or other Internet of things (IOT) device.

The obtaining processor 1010 may comprise one or more physical and/or virtual processors, and may be located within the remote server, and/or its functionality may be distributed or further distributed over multiple devices, including but not limited to the user's mobile phone 100, a docking unit 200, a vending machine 300, and the delivery device 10 itself. The obtaining processor may comprise one or more communication inputs, for example via network connections, and/or via local connections to local storage. The obtaining processor may also comprise one or more communication outputs, for example via network connections, and/or via local connections, for example to the estimation processor 1020.

The obtaining processor may comprise pre-processors or sub-processors (not shown) adapted to parse and/or convert obtained information into user factors where this information is not immediately usable as such; examples may include keyword or sentiment analysis of consumed media, for example to determine as a user factor a net positive or negative influence on an aspect of user state, or similarly keyword analysis of the user's calendar to determine locations and events, for example again to determine as a user factor a net positive or negative influence on an aspect of user state. Other inputs, such as ambient temperature or probability of rain, may similarly be converted to a scale appropriate to user factors, for example being normalized or classified according to influences on user state. Similarly noisy data may be processed to remove statistical outliers or to perform smoothing functions, or calculate averages or other statistical values, or the like. It will also be appreciated that such pre-processing or sub-processing may be performed at one or more devices within the user's delivery ecosystem on behalf of the obtaining processor.

The obtaining processor may thus be operable to generate and/or relay user factors for input to the estimation processor at varying degrees of abstraction from the original source material.

Hence optionally original source data may be enumerated, codified, classified, formatted, or otherwise processed, or simply passed through and provided as input to the estimation processor, so that there are potentially as many or more inputs as there are original sources of data. As will be appreciated from the description above, this may result in a large number of inputs.

Hence optionally one, some or all of the original source data may be any rated, codified, classified, formatted, or otherwise processed, or simply passed through as appropriate to an optional intermediate user factor generation stage of the obtaining processor; this may determine positive or negative influences from the submitted inputs on a specific subset of user factors that may be relevant to the user state but not directly or easily measurable, such as effects on dopamine and/or cortisol, heart rate, satiety, and the like.

Similarly such an intermediate user factor generation stage of the obtaining processor may combine inputs from similar classes to generate a class-level user factor for one or more of the classes of data described herein.

Hence as non-limiting examples, indirect or historical data could be summarized as how actively the user modifies or updates their device, or how receptive they are to such modifications, on a given scale. Neurological or physiological data could be summarized as how stressed the user appears to be, on a given scale, and/or their trajectory on that scale. Contextual data could be summarized as how sociably desirable use of the delivery device is currently, on a given scale. Environmental or deterministic data could be summarized by how likely the user is to want to use the delivery device in a given timeframe; and use-based data could be summarized as how frequently or deeply the user is or has recently used the delivery device.

It will be appreciated that in practice only source data from some or one of the classes may be available, and even where data from one class is available, a class-level user factor such as in the examples above may not be generated, or different kinds of class level user factor may be generated depending on the type of data received within that class (e.g. different subsets of individual user factors); similarly, class-level user factors may be generated for input to the estimation processor in parallel with individual user factors.

The contributing values and/or influences from different individual, subset and/or or class level user factors may then be presented as inputs to the estimation processor, with the selection of class, subset and/or individual user factors being chosen to give a good discrimination between different user states.

For example, galvanic skin response may provide a good indicator of a user's state, and is also responsive to nicotine as an active ingredient by reducing the response; as such it may optionally be a candidate for an individual source of data to be used as an input to the estimation processor. Other physiological measures to provide good discrimination include muscle tension (EMG), heart rate, skin temperature, brainwaves (EEG), and breathing rate. Any of these, where available, may be considered for inclusion as an individual source of data, optionally after being any rated, codified, classified, formatted or otherwise processed, alternatively or in addition combined in any combination with these or other user factors described elsewhere herein.

Similarly location, social setting, time-of-day, and hormonal levels are all good indicators of the user's state and may be candidates for use as individual sources of data as input to the estimation processor.

Hence more generally user factors may be obtained by or for the obtaining processor and provided to the estimation processor after any suitable parsing or processing, either individually and/or as combined subset or class values with one or more others (for example based on weighted contributions, statistical functions, trained machine learning outputs, look-up tables of precomputed correspondences between values of the obtained data and values of a target user factor, and the like), as for example individual, subset and/or or class level user factors.

Estimation Processor

The estimation processor 1020 is operable to calculate an estimation of user state, based upon one or more of the inputs received from the obtaining processor comprising or based upon obtained user factors. The calculation of an estimation of user state can be either explicit to generate an output reflective of a user's state prior to generating a proposed feedback action (which may be thought of as a two-operation process), or implicit to identify a proposed feedback action expected to alter a user's state (which may be thought of as a single operation process).

Like the obtaining processor, the estimation processor may comprise one or more physical and/or virtual processors and may be located within the remote server, and/or its functionality may be located in a device of the delivery ecosystem, such as the delivery device 10, or distributed or further distributed over multiple devices, including but not limited to the user's mobile phone 100, a docking unit 200, a vending machine 300, and the delivery device 10 itself. The estimation processor may comprise one or more communication inputs, for example to receive data from the obtaining processor 1010. The estimation processor may also comprise one or more communication outputs, for example to provide a proposed feedback action to the feedback processor 1030.

Explicit State Estimation

In an embodiment of the description, in a two-operation process the estimation processor initially explicitly estimates a state of the user in a first operation before then generating a proposed feedback action in response to the estimated state in a second operation. This estimated state may itself take the form of a single value or category, or may be a multivariate description of the user's state.

As non-limiting examples of a single value state, the estimated state may describe:

i. a stress level of the user;

ii. a degree of benefit the user is expected to subjectively experience in response to a unit consumption of a proposed active ingredient; and iii. a social flexibility score, indicative of how easily the user can currently use the delivery device and hence alter their state through modification of delivery;

As non-limiting examples of a state category, the estimated state may be:

i. one of a plurality of state classifications, all, some, or none of which may correspond to what are colloquially referred to as moods; hence for example happy, sad, low cortisol, medium cortisol, high cortisol, calm, stressed, receptive to change (for example willing to use their delivery device to alter their state), or unreceptive to change.

ii. one of a plurality of state classifications chosen to have a subsequent clear correlation with either inputs from the obtaining processor and/or an available feedback action, the classifications not necessarily fitting a notional category such as 'happy' or 'high cortisol', but having classification boundaries driven at least in part by their correspondence to either the available inputs from the obtaining processor or outputs for the feedback processor.

As non-limiting examples of a multivariate description of the user's state, the estimated state may comprise:

i. the user's stress level according to physiological indicators, and separately according to contextual indicators, together with an indication of their current social flexibility based on time-of-day, location, and/or proximity to specific individuals;

ii. an indicator of the user's physiological state based upon galvanic skin response and heart rate, together with current position in a hormonal cycle, and indicators of mental state derived from questionnaire and/or social media analysis.

These examples may be used to provide non-limiting illustrations of the operation of the estimation processor, as follows.

The estimation processor may use predetermined rules, algorithms and/or heuristics to convert input data from the obtaining processor into estimated states.

For example, a single value state such as a stress level of the user may be derived by applying a predetermined combination to a plurality of user factors, such as a weighted sum, with the result normalized according to the number of currently available inputs contributing to the sum.

Similarly a single value state such as the degree of benefit expected for the user may be derived by estimating the user's positive or negative emotional state based upon summing indicator values for positive or negative keywords or sentiments in on-line media recently consumed or produced, and positive or negative values associated with a classification of the user's location.

Likewise an estimated state category may be selected by template matching user factor values to predetermined values indicative of a given category, or similarly identifying a least-mean-squares error between user factors and a template of user factor values for each candidate category, optionally with different categories and greater error having different linear or non-linear weightings, reflecting their relative salience in identifying the category.

Finally as an example, a multivariate state may comprise deriving individual indications of state according to any of the above examples; hence a single value stress level may be generated as discussed above for each of physiological and contextual indicators, and a social flexibility value may be determined based upon scores previously associated with different times of day, location and class of specific individual (e.g., partner versus child); or a social flexibility classification may be based matching templates to such scores and/or values for the underlying input data.

Alternatively or in addition, the estimation processor may use look up tables to convert input data from the obtaining processor into estimated states.

In one instance, these look up tables may simply provide a precomputed implementation of the above predetermined rules, algorithms and/or heuristics, to avoid repetition of these calculations either at the server, or on a device within the delivery ecosystem that has limited processing capability but is acting as the estimation processor or sharing its role, such as the delivery device 10, or a dock 200, vending machine 300, wearable device 400, or associated phone 100.

In another instance, such look up tables may provide associations between input values from the obtaining processor and output values of user states, state classifications and/or multivariate states previously derived according to any suitable mechanism, such as for example feedback from extensive user testing, or as described later herein, the output of a machine learning system; again in this latter case, a look up table may potentially provide a computationally simpler facsimile of such a machine learning system by recording pairs of inputs and outputs for common values that may be easier to implement on devices within the delivery ecosystem having a comparatively low computational power.

Alternatively or in addition, the estimation processor may model correlations between input data and estimated states of the user. Such correlations may be due to causal links between a user factor and a user state, or a tendency for the user factor to accompany a cause of the user state, hence acting as a proxy, typically with particular degree of probability. Similarly such correlations may be due to the user factor and the user state both responding to a separate cause or circumstance in a manner that is sufficiently repeatable to form a correlation. Likewise such correlations may be due to the user state giving rise to the user factor. Hence more generally correlations relate to measurably predictable correspondences between one or more user factors (whether individual, subsets or class level user factors as output by the obtaining processor) and a user state (whether a single value, a classification or multivariate), typically either due to a causal link (in either direction between user factor and state), a common cause resulting in responses in user factor and user state with a repeatable relationship at least at a statistical level, and/or a measurable correspondence regardless of whether a direct or indirect causal link is known.

Where the estimation processor models correlations, it can be trained using a data set comprising as inputs data corresponding to the above described outputs of the obtaining processor, and as target outputs descriptors of a state of the user, whether single value, a classification, or multivariate, for example based upon a direct measurement of a user's state and/or user self-reporting regarding their state.

The specific means by which such correlations may be derived include any suitable technique for estimating such correlations, including a correlation map between inputs and outputs, where presentation of an input and output at the same time (or within a predetermined time window, if a temporal factor is included) results in a reinforcement of the link between the specific inputs and outputs (for example by increment of a connective weight). Once trained on the dataset, a new input will result, by virtue of the connective weights, in the activation to a greater or lesser extent of one or more candidate states correlating with that input; the candidate state with the strongest activation may then be chosen as the user state, or such states may be ranked by activation strength. It will be appreciated that in such a system, multiple input values may be provided simultaneously, corresponding to individual, subset of class level user factors as described elsewhere herein, and the generated outputs may correspond to a single value state, a classification, or a multivariate state with a number of values representing different aspects of the user state as described elsewhere herein being output.

A specific example of a correlation map is a neural network, and any suitable form can be considered.

More generally, any suitable machine learning system capable of determining a correlation or other predictable correspondence between one or more inputs and one or more outputs may be considered.

Given the above described dataset, such machine learning systems are typically supervised and may for example be a supervised classification learning algorithm, for example if the user state is a classification; or a supervised regression learning algorithm, for example if the user state is a single value or multivariate. Other forms of machine learning are also suitable, such as reinforcement learning or adversarial learning, or semi-supervised learning. Furthermore multiple independent machine learning systems separately trained on different or partially overlapping individual, subset or class level outputs of the obtaining processor can be ensembled to improve modelling results, for example to accommodate different configurations of source data due to different patterns of ownership of devices in the delivery ecosystem of different users, and different permissions and habits affecting the availability of online sources of information. It will also be appreciated that a mixture of different machine learning systems can be used in parallel, for example to generate a multivariate state of the user, with for example one or more different elements of the multivariate description been generated by different respective machine learning systems. These respective machine learning systems can be on separate hardware (e.g. based on dedicated neural processors) but more typically may be on the same hardware (e.g. software based machine learning systems that are loaded and run as required).

Meanwhile unsupervised learning algorithms may also be considered; hence for example associative learning may determine the probability that if one input or pattern of input is present then the user will be in a given state.

Examples of the above machine learning systems, in the forms of algorithms and/or neural networks, will be known to the skilled person.

Meanwhile machine learning may optionally also be used to prepare (e.g. pre-process) data, either at the estimation processor and/or in the obtaining processor; hence for example clustering (for example k-means clustering) may be used to classify a diverse set of inputs into a class level user factor of the type described previously herein. Such an approach may be used or also used for example to derive classifications for user states, as per the second example of a state category classification described previously herein, in response to inputs from the obtaining processor or available feedback actions of the feedback processor.

Similarly as a preparatory operation at the estimation processor and/or obtaining processor, dimension reduction, such as principal component analysis, may be employed to reduce the number of inputs whilst retaining information having a significant correspondence with the user state.

Hence in summary the estimation processor, if generating explicit estimates of user state, uses a repository for the correspondence between available inputs from the obtaining processor and the estimated states, where that repository for the correspondence may be embodied in algorithms, rules or heuristics, and/or in one or more look up tables, and/or in one or more trained machine learning systems.

In each case, the result is an estimation of the user state, which may take the form of a single value, a category, or a multivariate description/representation of the user state as described previously herein.

Meanwhile the operation of the estimation processor if generating implicit estimates of user state, is described later herein.

Feedback Proposals from an Estimated State

As noted previously herein, the estimation processor may operate in a two-operation process; in the first operation estimating a user state from inputs comprising one or more user factor or data derived from such user factors by the obtaining processor, as described previously herein, and in the second operation generating a proposed feedback action expected to alter a user's state, as will be described below.

In principle, the second operation may be implemented by the feedback processor rather than the estimation processor, or may be shared between the feedback processor and the estimation processor. Alternatively the feedback processor may simply receive the proposed feedback action. In any case, the feedback processor may then select the feedback action (either by default if only one is proposed, or selecting one or more if a plurality are proposed), or optionally act to cause one or more feedback actions proposed by the estimation processor to occur in an appropriate manner within the delivery ecosystem.

For the purposes of explanation, the second operation is described herein as occurring within the estimation processor.

The two-operation process may be chosen for practical reasons; for example, training sets for use in modelling the correspondence/correlation between user factors or their derivations by the obtaining processor and user state may be easier to generate or acquire than training sets for use when directly modelling the correspondence/correlation between user factor based inputs and proposed feedback actions, because the user's state may be either directly measurable, or straightforward for a user to report.

Similarly it may be easier to generate a training set determining the correspondence/correlation between a measurable and/or self-reported user state and a proposed feedback action, based for example upon user questionnaires ranking feedback actions for given states, and/or upon the subsequent effectiveness of an implemented feedback action in altering the state of the user toward a more desirable state, as measured and/or reported by the user. Typically a more desirable state is one which improves the user's subjective sense of well-being and/or moves physiological or neurological indicators of the user's state toward a preferred norm (for example reducing elevated heart rate, galvanic skin response, elevated skin temperature, and/or breathing rate, and the like).

The input for the second operation will typically be an estimation of the user state, represented by a single value, a category, or a multivariate description as described previously herein, or a plurality of these if multiple states are estimated (for example with varying degrees of activation/strength of correlation in response to the inputs of the first operation). Optionally, inputs to the second operation may also comprise one or more user factors and/or inputs as provided by the obtaining processor; for example, as described elsewhere herein certain physiological measurements may be useful indicators/proxies for the user state, such as galvanic skin response, heart rate, breathing rate, skin temperature and the like. Hence optionally one or more of these or any other inputs to the first stage, may also be provided for the second stage in conjunction with the or each estimated state.

In any event, as with the estimation of the user state, the generation of a proposed feedback action may use any suitable mechanism that embodies a correspondence/correlation between the estimated user state and the proposed feedback action.

As noted previously, this may include predetermined rules, algorithms and or heuristics to convert estimated states into proposed feedback action.

- For example, a single value state (such as degree of stress) may drive a corresponding proposed feedback action, such as increasing the proportion of active ingredient within an inhaled unit volume of generated aerosol, which in turn may be achieved by modifying heater, air flow, reservoir and/or other payload storage settings, and the like, which as described later herein may be managed by the feedback processor. The relationship between the degree of stress and the change in active ingredient may be linear or non-linear, or may change qualitatively at different values, for example not changing at all for low levels of stress, have a linear relationship for medium levels of stress, and have an asymptotic relationship for high degrees of stress up to a maximum proportion of active ingredient, and for example at or near this maximum also modifying a behavior of the user interface of the delivery device or other device within the ecosystem, such as issuing a warning or calming message on the user's phone.
- Meanwhile for example a single category state may have a corresponding proposed feedback action.
- Finally for example a multivariate state may result in a corresponding proposed feedback action being based on weighted or unweighted contributions from the different elements of the state description, and/or different feedback actions may be proposed based on overlapping or non-overlapping subsets of the elements of the state description. Hence for example if the state description suggests that the user is stressed and are in a work environment, then the feedback action may assume that they are implicitly stressed because they are in the work environment, but are currently unable to increase their intake of active ingredient, and therefore issue a message on a UI of the delivery device or other devices in the ecosystem, such as the user's phone, to suggest the user that they take a break. Meanwhile if the user is stressed but not in their work environment, then the feedback action may be similar to the degree of stress example above, resulting in an increase in the proportion of active ingredient delivered to the user.
- As noted above, any one of these may also be accompanied by one or more inputs to the first operation.

Again like the estimation of user state, the estimation processor may alternatively or in addition use look up tables to convert state estimation data into proposed feedback actions.

Alternatively or in addition, again like the estimation of user state, the estimation processor may model correlations between estimated user states and proposed feedback actions, and the use similar techniques to do so.

Where the estimation processor models correspondences/correlations, it can be trained using a data set comprising as inputs data corresponding to the estimated user state (for example in the form of single values, classifications, or multivariate descriptions, or a combination of these) and optionally also inputs from the obtaining processor as described previously herein, and as target outputs proposed feedback actions.

The proposed feedback actions are discussed in more detail later herein, but may typically comprise at least one type of action and optionally one or more variables characterizing the performance of that action. Hence for example a change in temperature is a type of action, and an increase or decrease, or amount of increase or decrease, would represent a variable characterizing the performance of that action. Similarly modifying active ingredient concentration in the aerosol is a type of action, and an increase or decrease in concentration, or an amount of increase or decrease, would represent a variable characterizing the performance of that action.

Hence as a non-limiting example in the context of a machine learning system, different output nodes may represent different types of action, and the values of those nodes may represent either a flag indicating selection of that feedback action, or a value relating to a variable of that feedback action, depending on how the system is trained. It will also be appreciated that multiple output nodes may be associated with one or more types of action in a machine learning system, depending on the training regime.

It will be appreciated that potentially a plurality of feedback actions may be indicated in response to an estimated user state. In such circumstances, the feedback processor may subsequently determine whether to select just one feedback action, for example based upon the degree of change caused by the action as implied by its associated variable or variables, or implement multiple feedback actions in parallel or sequentially, in the latter case optionally a sequence determined by a predetermined order, or again responsive to the strength of activation of a flag output node for each feedback action, and/or the degree of change implied by each action's associated variable or variables.

It will also be appreciated that to train such a machine learning system, measured and/or reported user states could be provided as inputs, and respective proposed feedback actions could be provided as targets, with actions and values selected according to their reported efficacy during user trials for users having the corresponding user state; again in this case efficacy or effectiveness typically relates to the user's perceived improvement in state, and/or a change in neurological and/or physiological state toward a predetermined norm or preferred state.

Optionally as first training phase, simulated states and corresponding feedback actions could be used to provide initial training (for example based on questionnaire results as described previously), with a proportionally smaller cohort of real-world training data then being used to refine the model.

Optionally, feedback from the user themselves as to the efficacy and/or suitability, desirability, practicality etc., of any feedback actions could be further used to refine the model and effectively personalize it to the user. Again this feedback may be reported by the user for example via a user interface on a device within the delivery ecosystem such as the delivery device or their phone, and/or based on measurements of neurological and/or physiological response. Where plural feedback actions are implemented or indicated, optionally the user may rank them in order of preference.

In summary, the two-operation process, comprising an explicit estimation of user state as a first or interim operation, may be of use where these operations better fit the available underlying empirical data sets used to model the correspondences/correlations, whether this is done by rule-based techniques or machine learning.

Objectively, the operation of the estimation processor in this mode is thus to take inputs from the obtaining processor, typically in the form of different individual, subset and/or or class level user factors, and output one or more proposed feedback actions either simply identifying the action in a manner similar to a flag, and/or identifying the degree of relevance of that action to the estimated state based on the activation level and output corresponding to the proposed feedback action, and/or indicating a change or amount of change of one or more variables that at least in part characterize the proposed feedback action.

The explicit estimation of the user state is thus typically an internal, interim operation. However it will be appreciated that this estimate could be relayed to the user for their information, and optionally the user could modify the estimate, particularly where the estimate or a component of the estimate in a multivariate description relates to a subjective measure or to a proxy of a subjective measure such as the user's sense of stress. Hence for example the estimate could be displayed on a user interface of the user's mobile phone, and the user could use this information to self-assess, and make changes to the estimate as a result. The modified estimate of the user's state could then be used together with or instead of the originally generated estimate in the second operation to identify/generate a proposed feedback action that may be more accurate than the proposal based on the original estimate of the user's state.

Furthermore, any changes made to the estimate of the user's state could be used to update and refine the model of the first operation, and indeed for certain machine learning techniques, a lack of correction by the user may similarly be taken as a positive reinforcement of the estimate for the purposes of training.

As mentioned previously herein, if further training is not desired, then optionally the relationships between input and output values derived by the machine learning process may be captured in one or more look up tables, which may be computationally simpler to use (though may occupy more memory).

Implicit State Estimation

In an embodiment of the description, rather than using the two-operation process described above, the estimation processor performs a single operation process that implicitly estimates a state of the user as part of the relationship between individual, subset and/or or class level user factors provided as input by the obtaining processor, and proposed feedback actions generated as an output and typically expected to alter a user's state.

Hence an estimation processor (1020) adapted to calculate an estimation of user state based upon one or more of the obtained user factors may equally be an estimation processor (1020) adapted to identify/generate a proposed feedback action state based upon one or more of the obtained user factors; in this case the user state is implicit in the relationship between the user factors and the proposed feedback action, which is expected to alter the implicitly estimated state of a user.

In a similar manner to the two-operation process described previously herein, the estimation processor may use predetermined rules, algorithms and/or heuristics to convert input data from the obtaining processor into estimated states. These may for example combine the processes for the two separate operations of the explicit state estimation embodiments, and/or refine some or all of the rules, diagrams and/or heuristics in response to the single operation nature of the implicit state estimation approach, or may be derived from scratch for the singe operation process.

Again like the two-operation process, the estimation processor may alternatively or in addition use look up tables to convert input data into proposed feedback actions. Again these may be concatenations of look up tables from the two-operation approach, and/or may be further processed to provide single operation look-up tables, or may be derived from scratch for the singe operation process.

Again like the two-operation process, the estimation processor may alternatively or in addition use machine learning. In this case for example, inputs used in the first operation of explicit state estimation, and targets used in the second operation of generating proposed feedback actions from the estimated steps, may be used to train a machine learning system that identifies measurable correspondences between them.

It will be appreciated that to present corresponding inputs and targets for training purposes, the training set should have captured this correspondence; as noted previously herein, it may be that datasets exist for the inputs and a user state, and user states and effective feedback actions; consequently inputs and feedback actions can be married for training purposes based upon the common user state value, class or multivariate descriptors as appropriate; clearly also where the training datasets were collected by users for whom user factors were measured and/or self-reported, user states were measured and/or self-reported, and subsequent efficacy and/or suitability, desirability, practicality etc., of feedback actions were measured and/or self-reported, then these self-consistent sets of input user factors (as provided by the obtaining processor) and target feedback actions can be used for training.

Alternatively or in addition, a two-operation system with explicit state estimation, which has been trained on separate datasets, and/or uses respective rules, algorithms and/or heuristics from the two operations, and/or uses look up tables from the two operations, can be used as a data source.

For example, a single operation look-up table may be created by running through the first and second operations of look-up tables or rules, algorithms and/or heuristics, and/or machine learning systems for a two-operation estimation to provide look up links between inputs as provided by the obtaining processor, and proposed feedback actions identified/generated by running through the two operation process using those inputs.

Alternatively or in addition, a single operation machine learning system may be trained by running through the first and second operation of look up tables or rules, algorithms and/or heuristics, and/or machine learning systems for a two-stage estimation to provide inputs as provided by the obtaining processor, and provide as targets for training proposed feedback actions identified/generated by running through the two operation process using those inputs.

Optionally, a single operation machine learning system trained in this manner may then have its training refined using additional data, such as a combined training set as described above and/or, in a similar manner to that described previously herein for the operation scheme, data received from one or more users during use of the user feedback system.

It will also be appreciated for example that a training set may be based directly on capturing the desired input and target values rather than using an amalgam of datasets or processes.

It will be appreciated that for either the two-operation approach or the single operation approach, training data may be gathered using one or more devices in the delivery ecosystem, for example to build a training set relating user factors to user states. Such a training set may be generated using a version of the user feedback system that does not generate a proposed feedback action, but simply gathers the user factors and user state information. Similarly a training set relating user states to proposed feedback actions may initially be based upon asking users, for whom their state is known (e.g. measured/reported) to rate proposals for feedback actions, for example via a user interface on their phone as part of a user testing scheme. Hence in this case the feedback system may propose feedback actions and select one or more of the proposed actions, but in different versions or modes may either present the selected proposed feedback action(s) to the user for evaluation (for example via a user interface) for example during a training-data gathering phase or a calibration phase (for example to characterize the user within a subgroup to which responses may be better tailored, as disclosed elsewhere herein), or may cause the selected proposed feedback action(s) to be implemented, modifying of one or more operations of at least a first device within the delivery ecosystem, responsive to the estimation of user state (whether explicitly or implicitly modelled), in a manner expected to alter the estimated state of a user. Training data relating user factors to proposed feedback actions may be obtained in a similar manner.

Hence such datasets may be obtained using a version or mode of the user feedback system that as noted above does not actually cause a modification to one or more operations of a device in the ecosystem (optionally except for eliciting a response from the user, e.g. for training data purposes).

This preceding generation of the user feedback system, or training/refinement mode of the user feedback system, could thus comprise an obtaining processor (1010) operable to obtain one or more user factors indicative of user state, and operable to obtain user state data (for example based on measurements similar to those of user factors, and/or self-reporting by the users), and or feedback action preference/efficacy data; the estimation processor would then comprise a training or development phase in which the correspondences/relationships/correlations between inputs based on the user factors as described previously and targets based on the user states (in the two-operation scheme) or the proposed feedback actions (in the single-operation scheme) are modelled as described previously, for example once a sufficient corpus of data had been amassed.

Alternatively or in addition, in such a preceding generation and/or in a training mode of a feedback system, the delivery device and/or other participating devices in the delivery ecosystem may consequently only upload data to the obtaining processor, but not download feedback actions (or optionally any other data) from the feedback system.

Similarly, in either such a preceding generation and/or in a training mode of a feedback system, and/or in providing improved or supplementary input for the feedback system, then as mentioned elsewhere herein user factors such as from neurological/physiological data (e.g. from biometric sensing), motion and/or location user factors (e.g. from touch, accelerometer or GPS sensors), contextual user factors, and/or any of the other user factors disclosed herein may be accompanied by direct input on the user's state as reported by the user. This may be used for the generation of a training set, as described previously, but alternatively or in addition the user's reported state may be treated as a user factor by the obtaining processor, or directly by the estimation processor. In principle the user's reported state may optionally be used in lieu of an explicit state estimation by the estimation processor, but it is possible that at least in some cases the user's reported state will be approximate compared to what may be derivable, or estimated from some measurements (if these are available), or the user may not be informed by all the facts available to the feedback system. Furthermore, some users may normalize their state and self-report in a biased manner, particularly for pathological states such as depression. Hence optionally the user's direct input on their state may be used in conjunction with one or more other user factors from the obtaining processor as described above as input to the estimation processor, in the first (or only) operation as described above. Optionally, alternatively or in addition the user's direct input on their state may be used in conjunction with an estimation of their state as input to the second operation of the estimation processor, if the two-operation technique is used.

Other variations in training and input may also be considered. For example it will be appreciated that as noted previously herein, different user factors operate or vary over different time scales. Consequently for either the two-operation approach or the single operation approach for the estimation processor as described herein, user factors that are not expected to have changed within an interval between successive operations of the estimation processor may be stored and re-used (for example in storage 1012), rather than being re-obtained.

Furthermore, some parts of the estimation model relating to these longer term factors may not need to be re-run if the outcomes for those factors are expected to remain the same. This may be straightforward for rule, algorithm and/or heuristic methods, and/or look-up tables, but for a machine learning system it may require a modified architecture; for example a two-stage ML or multi-layer system may be trained on all inputs, but subsequently run with inputs or outputs relating to long-term user factors clamped, and the previously computed intermediate results of that part of the ML system fed into the remaining part of the ML system in conjunction with newly generated intermediate results from user factors with shorter time frames.

It will also be appreciated that as noted previously herein, different users may have different combinations of devices within their delivery ecosystem, and/or different combinations of these devices may be active at any one time; similarly, different users may have greater or lesser presence on social media, or use their digital calendar to a greater or lesser extent, and the like. Consequently the user factors available to the obtaining processor and hence also the inputs available to the estimation processor may differ from user to user, and/or from time to time. Accordingly, the estimation processor may use different models (explicit or implicit, as discussed above) to propose feedback actions, depending upon the inputs available. Alternatively or in addition, where an input to a model is missing, a neutral input value may be provided so as to reduce or remove the influence of that missing input on the feedback action proposed. The number of different models provided by/for the estimation processor may therefore depend upon the number of data sources assumed for a model (with more sources or more diverse sources making the model potentially more fragile), and the robustness of the model to the replacement of inputs with placebo/neutral values where an input is currently unavailable; in this latter case it will be appreciated that some inputs may be more critical than others, so at least some individual inputs may be required for a model to run. Hence depending upon the complexity and robustness of the model, it may be that only one model is needed, or a suite of models anticipating different scenarios. Optionally, a subset of all available models is selected for a user depending upon the devices known to exist in their delivery ecosystem; meanwhile new models may be added when new devices join the delivery ecosystem, whether permanently for example in the case of the user buying a new dock 200, or temporarily for example in the case of the user interacting with a vending machine or point-of-sale device.

Estimation Processor Output

Whether a single operation or two operation process is used, and whether the estimation for any operation is based on rules, algorithms, and/or heuristics, look up tables, and/or machine learning, the output of the estimation processor is a proposed feedback action.

Possible feedback actions differ qualitatively and/or quantitatively.

Hence for example they may vary qualitatively based on whether they relate to modifying the generation of aerosol for the user (whether in response to current circumstances or pre-emptively); modifying the user's interaction with the delivery device or system, either during inhalation or between inhalations; modifying the user interface of the delivery device or system; reminding the user to use or change their use of a delivery device or system; recommending an operation or selection of a delivery device or delivery device consumable; and/or recommending/activating/modifying the operation of a device that is not directly related to the delivery of active ingredient, but may nevertheless change the user's state, either directly (for example through biofeedback) or indirectly (for example by activating noise cancellation in a user's headphones).

Hence more generally feedback actions may fall into categories that are behavioral, focusing on altering actions and/or habits of the user to change their state; pharmaceutical, focusing on how one or more active ingredients delivered to the user may change their state; and non-consumption interventions, focusing on alternative first or third party options (i.e. relating to the delivery device or other devices in the delivery ecosystem or elsewhere) to change a user's state.

Meanwhile proposed feedback actions may vary qualitatively depending on the extent to which the effect of the feedback action is desired to make a positive change in the user's state; hence for example in the delivery device a change to heater temperature, payload aerosolization, payload composition, or the like may comprise a quantitative value indicating the degree of change, or class of change, as appropriate. Similarly modifications to a user interface in the delivery device or another device of the delivery ecosystem may comprise incremental operations relating to the number of user interactions required or prompted with the delivery system, and the nature of those user interactions; for example running through five categories, with the first category having no notifications to minimize interruption of the user, a second category only having critical notifications such as for low battery or low payload, a third category corresponding to a default in which critical and non-critical notifications are provided, a fourth category further including recommendations and/or prompts to engage the user with other features of the user interface, and a fifth category additionally including an audible tone. These five categories may be selected according to the user state on a scale of how stressed they are (for example with minimal notifications for high stress), and/or how bored they are (for example with high notification for high boredom).

As noted previously, the type of feedback action, and/or the amount or class of change, if appropriate, may be identified according to rules, algorithms, and/or heuristics, look up tables, and/or machine learning as appropriate.

Similarly as noted previously, where more than one type of feedback action, and/or more than one amount or class of change is calculated/estimated to be an appropriate response to the user factors/user state, optionally multiple feedback actions may be proposed accordingly, or the top N feedback actions may be selected based for example upon strength of activation, where N may be one or more.

Feedback Processor

The feedback processor 1030 is operable to implement one or more proposed feedback actions, thereby causing modification of one or more operations of a device within the delivery ecosystem, responsive to the estimation of user state.

Hence the feedback processor may act to cause the feedback action or actions proposed by the estimation processor to occur in an appropriate manner within the delivery ecosystem.

The feedback action or actions are typically implemented in a manner expected to alter the estimated state of a user. This user may be considered a generic, average, notional user; it will be appreciated that the model or models upon which the generation of the proposed feedback action(s) is/are based are typically developed or trained using data from a corpus of users, and hence relate to changing the state of a generic, average, or notional user.

However, typically this will nevertheless similarly alter the state of the particular user of a respective delivery device, on the basis that most users are likely to respond in a similar manner to these changes.

However as described elsewhere herein, if the feedback system can receive further feedback from the individual user (for example by measurement or self-reporting) as to the efficacy of proposed feedback actions, then optionally the system can become increasingly tailored towards the particular user, for example through supplementary training and/or refinement of parameters, and hence implement feedback actions responsive to the estimation of user state in a manner expected to alter the estimated state of the particular user. Similarly, separate rules, algorithms, and/or heuristics, look up tables, or machine learning systems may be generated for different user groups, for example based on demographics and/or patterns of response to feedback actions, so that the proposed feedback actions are better tailored to a particular user falling within one of these groups, even if measured or reported assessments of feedback efficacy are not available from the particular user, or are too sparse to effectively refine the training of a machine learning system or alter the parameters of an algorithm etc., to personalize its response to them.

Like the obtaining processor and the estimation processor, the feedback processor 1030 may comprise one or more physical and/or virtual processors and may be located within the remote server 1000, and/or its functionality may be distributed or further distributed over multiple devices within the delivery ecosystem, including but not limited to the user's mobile phone 100, a docking unit 200, a vending machine 300, and the delivery device 10 itself. The feedback processor may comprise one or more communication inputs, for example to receive data from the estimation processor 1010, and one or more communication outputs, for example to communicate with the delivery device 10, and/or another device within the delivery ecosystem 1 such as those listed above, or any other device that may participate in a feedback action.

In particular, the feedback processor may optionally comprise a selection and notification sub-processor (not shown) which may be located at the server and/or at a device within the delivery ecosystem with suitable computational power, such as a vending machine or mobile phone, to optionally select one or more feedback actions and select one or more respective devices within the ecosystem for implementing one or more feedback actions; and optionally an action implementation sub-processor (not shown) at one or more respective devices within the ecosystem for managing the implementation of a feedback action. Optionally, the action implementation sub-processor may be considered a separate processor to the feedback processor.

Herein, references to the selection and notification sub-processor and the feedback processor, or the action implementation sub-processor and the feedback processor, may each be considered interchangeable; it will be appreciated that whilst these sub-processors may be complementary hardware to the feedback processor, and/or effectively share a role of the feedback processor, they may equally be functions of the feedback processor operating under suitable software instruction. Meanwhile as noted above, optionally at least the action implementation sub-processor may be a separate processor to the feedback processor, for example communicating with the feedback processor via the Internet.

Selection and Notification

Optionally, the selection notification sub-processor may select one or more feedback actions generated by the estimation processor in a manner as described previously herein, if the estimation processor indicates more than one feedback action may be appropriate. Clearly, if only one feedback action is proposed, then as a default this would be selected.

For a selected feedback action, the selection notification sub-processor may then select which device or devices within the delivery ecosystem should implement the feedback action, and formulates a command/notification/instruction for the or each device characterizing the type and/or amount of the feedback action. It will be appreciated that where a device is only capable of one feedback action, then the type can be implicit in the act of notification, and similarly where a device is only capable of one amount feedback action, then the amount can be implicit in the act of notification. Any device within the delivery ecosystem could potentially comprise a feedback means. It will be appreciated therefore that potentially the device or devices that provide user factor data to or for the obtaining processor within the delivery ecosystem are different to the device or devices implementing the or each feedback action.

Optionally, the selection notification sub-processor may poll devices within the delivery ecosystem to determine their availability for the purposes of providing a feedback action. For devices that may be accessible by the processor, for example by the Internet, then devices registered in association with the user or the user's delivery device (such as for example the delivery device 10, mobile phone 100, wearable device 400, docking device 200) may be polled directly.

For devices that may only be accessed via an intermediary device, for example via Bluetooth® connection to an accessible device, the accessible device may be asked to poll such indirect devices. Hence for example the selection notification sub-processor may cause/request the user's mobile phone 100 to poll a delivery device 10, wearable device 400 or docking device 200, if these are only accessible via a local wired or wireless connection.

For devices that are not formally associated with the user or only intermittently associated with the user, such as a vending machine 300 or other point of sale system, the selection notification sub-processor may receive location data from a device within the delivery ecosystem associated with the user, such as their mobile phone 100 or delivery device 10, and compare this with a registered or reported location of the vending machine 300; if the locations are within a threshold distance of each other, then the vending machine may be considered part of the delivery ecosystem whilst that condition holds true. Alternatively or in addition, the selection notification sub-processor may instruct an accessible device to either poll for any compatible vending machines, or broadcast a Bluetooth beacon identifying the accessible device, for example using a single-use ID so that the accessible device is identifiable without revealing details of the user or their associated devices; such an ID may comprise a component identifying the purpose of the ID to enable detection by the vending machine, followed by the single use component unique to the user or their associated device; a compatible vending machine in accordance with embodiments of the present invention may then optionally recognize the single use ID and relay it back to the selection notification sub-processor, thereby informing it that the user has accessible devices within local wireless range of the vending machine. It will be appreciated that whilst the above makes reference to a vending machine, this is an example for the purposes of explanation, and these techniques may apply to any device not formally associated with a user or only intermittently associated with them, such as a car or train, a WiFi® or Bluetooth® hotspot in a shop, a smart TV, or the like.

Optionally, devices outside the user's own deliver ecosystem may be selected. For example, a delivery device and/or a phone or other device of a friend or family member associated with the user (for example following registration of these people by the user) may be used to inform that friend or family member of the user's status, so that the friend or family member can intervene. Optionally the user can set the conditions under which this occurs, and/or which friends or family members are notified. Similarly, devices within a predetermined proximity of the user may be selected. For example, if the user is in a good mood, compatible devices within a predetermined radius of the user may all synchronize a feature such as a color of a light, to signal to these users that there is scope for an enjoyable social encounter.

Using one or more of these techniques, the selection notification sub-processor may thus determine what devices are currently available to deliver a feedback action.

Typically, a feedback action will be specific to a particular device within the delivery ecosystem or a pair of devices cooperating to fulfil a function; consequently, for a proposed feedback action or selected feedback action, optionally the selection notification sub-processor may only poll the device or devices within the delivery ecosystem that are relevant to that feedback action.

Similarly, it will be appreciated that certain devices within the delivery ecosystem may provide input data to the feedback system that is used to generate the proposed feedback action; consequently such input activity from devices may be logged as indicating their accessibility, and/or it may be implicit from the proposed feedback action that certain devices are currently accessible to the feedback system; in either case, a poll of the devices may not be necessary, or the receipt of input data may be treated as an effective poll result if a polling scheme is in place.

In the event that the device or devices relevant to that feedback action are not available (e.g. do not respond to the poll), then optionally the feedback processor/selection notification sub-processor may choose the next proposed feedback action in the top N feedback actions, if multiple feedback actions were proposed by the estimation processor. If no relevant device is available for a feedback action, then the feedback processor may not implement any feedback action, and/or send a notification to the user to that effect, for example via a user interface of the user's phone, or if the user's phone, as the accessible device for linking to other devices within the ecosystem, is not available, then notifying the user via a text or similar other mechanism that will reach the user once they are contactable again. Similarly, if there is no effective communication currently available between the feedback processor and the relevant device or devices, or (depending on where the feedback processor is at least in part located), there is no effective communication between the feedback processor at a relevant device or devices and the estimation processor or other parts of the feedback system, then the relevant device or devices may default to a normal otherwise default delivery or other default behavior suitable to that device.

In the event that the device or devices relevant to a feedback action are available (i.e. do respond to the poll, or have responded to a poll within a predetermined preceding period of time during which it can be assumed the device is still accessible, or have contributed input data within a predetermined preceding period of time), then the feedback processor will transmit one or more commands to the device or devices for implementing the feedback action as proposed by the estimation processor.

As noted above, the nature of the commands may depend upon the proposed action and the target device or devices. In some cases, the simple existence of the command will be sufficient to specify the proposed action, for example to turn a device on when it is off. In other cases, the command will need to specify the type of feedback action, for example in relation to changing heater function, payload type, user interface behavior or the like within the delivery system. In either of these cases, the command may need to specify the amount of feedback action, for example to specify the change in temperature, the concentration of active ingredient or flavoring within the payload, or selected parameters for the user interface.

As noted above, the command may be directly to an accessible device, or may be to request that an accessible device relays a command to another device within the ecosystem, or itself issues a command to such a device; for example the feedback processor may instruct the user's mobile phone 100 to issue commands to the delivery device 10. Further degrees of indirection may be envisaged, such as the user's mobile phone issuing commands to a dock 200, which in turn may modify settings of the delivery device when it is docked (for example to charge power or payload). It will similarly be appreciated that the feedback processor may issue commands of different kinds to different devices; hence for example a command may be issued directly to the mobile phone to change aspects of its user interface, and to a dock 200 (either directly if it is capable, or via the phone), causing it to change a composition of a payload to be provided to the delivery device, and also change one or more settings on the delivery device when it is docked. It will be appreciated that other permutations of commands such as these, whether direct, indirect, or a mix of the two, can be envisaged within the delivery ecosystem.

As described elsewhere herein, will be appreciated that different feedback actions may relate to behavioral, pharmaceutical and/or non-consumption aspects of the delivery ecosystem.

Behavioral feedback actions are typically focused on altering actions and habits of the user relating to operations of, and/or interactions with, a device within the delivery ecosystem other than operations relating to an amount or nature of an active ingredient delivered by the delivery device itself, although this can occur in parallel. Examples may relate to the use of changes in flavor or flavor concentration, changing vapor mass delivery to modify inhalation behavior; modification to scheduling schemes or reminders relating to delivery device usage or correlated with delivery device usage; changes to user interfaces, whether on the delivery device on another device in the delivery ecosystem, in terms of information provided, mode of feedback (e.g. haptic and/or visible such as colored lights, graphical themes, and/or messages); for example providing a traffic light UI display on the delivery device, such as an LED, to alert the user to how they are using the device), and the like.

Pharmaceutical feedback actions focus on pharmaceutical interventions to change the state of the user, and typically relate to interventions based on active ingredients, such as the amount or type, and when these are changed (for example reactively or pre-emptively, for example based upon correlations between current user factors and future user states or feedback actions), and the like. Such acts can also relate to selecting alternative modes of consumption, for example switching from vaping to snus or vice versa.

Non-consumption feedback actions typically relate to activating/controlling or simply recommending the use of devices not specifically related to the consumption of the active ingredient, such as aromatherapy systems/steamers, biofeedback devices, headphones (for example activating noise cancellation, or modifying volume or music selection), vehicle use (for example stress warnings, or route selection/reselection to longer but less congested or slower routes), and the like.

The selection notification sub-processor may be comprised of one or more real or virtual processors, and its functionality may be located or distributed within the server and/or one or more devices within the delivery ecosystem as appropriate.

Action Implementation

The action implementation sub-processor may be optional; for example some devices may accept commands directly with no further interpretation or processing required. In this case the action implementation sub-processor may be either thought of as not required, or having its role implemented by the feedback processor/selection and notification sub-processor.

Meanwhile, in some cases the role of the action implementation sub-processor may in fact pre-exist within the device, which for example is capable of interpreting user interface commands to implement changes to the operation of the device; in this case, the commands from the feedback processor may optionally simply replicate such user interface commands.

In other cases, the action implementation sub-processor may be separately provided, for example by adapting a conventional processor according to suitable software instruction. Such an example may be an app on a user's mobile phone, operable to receive commands and modify one or more of aspects of the mobile phone and/or the app on the mobile phone, the delivery device, and/or one or more other devices in the delivery ecosystem. Similarly, a dock 200 for the delivery device may comprise such an action implementation sub-processor, as may some varieties of delivery device.

The action implementation sub-processor operates to implement the feedback action on the or each relevant device. Hence for example if a command relating to a feedback action describes changing heater temperature of the delivery device, then the action implementation sub-processor may change the power supply to the heater, and/or a duty cycle of the heater, to implement the specified change.

Similarly for example if a command relating to a feedback action describes reducing ambient noise levels for the user, then the action implementation sub-processor for a pair of noise cancelling headphones may activate the noise cancelling function; the action implementation sub-processor for the user's mobile phone may reduce the volume level of music being played into those headphones, and display a message to the user suggesting that they seek to avoid sources of noise in their environment.

The specific actions implemented by respective sub-processors may thus depend on the nature of the proposed feedback action and the nature of the device within the delivery ecosystem, but will typically represent a direct translation of the proposed feedback action into the mechanism by which it may be enacted within device.

As noted previously herein, feedback actions may be accompanied or followed up by requests or opportunities for the user to report on their efficacy. Alternatively or in addition, feedback actions may be accompanied or followed up by positive reinforcement of the expected state change, for example through a message on a UI, or a change of interface color, haptic response or the like, or for example a positive goal being met in an app for a wearable. The reinforcement may be a simple message indicating that the feedback has occurred, or may be based upon measurements, for example to report that the user's heart rate has lowered, or to confirm that an action has worked well (by changing the user's state, typically as evidenced by a change to one or more user factors, or as self-reported by the user). The perception and/or expectation of a change in state engendered by such positive reinforcement can increase the effectiveness of at least some feedback actions.

The action implementation sub-processor may be comprised of one or more real or virtual processors, and its functionality may be located or distributed within the server and/or one or more devices within the delivery ecosystem as appropriate.

Processors

As noted previously, the obtaining processor, estimation processor, and feedback processor (and any sub processors) may comprise one or more real or virtual processors located within one or more servers and/or within the delivery ecosystem. Furthermore it will be appreciated that the demarcation of roles described herein is not fixed; for example the obtaining processor may receive information directly indicative of user state (for example by user self-reporting), and so the first operation of a two operation process by the estimation processor could be bypassed or supplemented by the obtaining processor; similarly in this case, the feedback processor may, for example, look up a corresponding proposed feedback action. Hence in this example, the role of the estimation processor is carried out by the obtaining processor and the feedback processor. Hence more generally these processors are representative of tasks that may be implemented by any processor under suitable software instruction, and can equivalently be considered to comprise a data gathering task, a feedback proposal task (whether or not based on an explicit estimation of the state of the user), and either a feedback training task or a feedback delivery task.

In an embodiment of the description, as noted elsewhere herein data may be collected from sensors on the delivery device and transmitted to a companion device within the delivery ecosystem such as a user's phone. The data may optionally undergo at least some pre-processing by the delivery device prior to transmission. As noted elsewhere herein, such sensor data from the delivery device may then be associated with data from other sources (e.g. information relevant to the user's state before, during and/or after the recording of the sensor data, such as the previously mentioned environmental, deterministic, contextual, neurological, physiological, indirect, and historical data) to generate multiple source associated data. This data may be sent to a backend server (e.g. at least part of the obtaining server function occurs at such a server). Alternatively the data may be processed with the smartphone operating as the obtaining processor, and the function of the estimation processor may be implemented on one of the phone, the back end server, or a mix of the two. In this case the function of the feedback server may similarly be implemented on one of the phone, the back end server, or a mix of the two (for example depending on the nature of the feedback or follow-on activities; actions such as sending notifications or product requests may be conducted by the back end server in one embodiment, or the phone in another). The combination where all three processors are implemented by the smartphone has the advantage of privacy for the user because no data is sent to a back end server. Alternatively for example, the function of the estimation processor may be performed by the server as this is likely to be computationally complex; meanwhile the inputs to the estimation processor may be machine readable only and optionally associated with an anonymized request (e.g. a single use request number), so that the data can be processed without the user of the back end server being able to determine the inputs or estimated state of a particular user.

SUMMARY EMBODIMENTS

In a summary embodiment of the present description, a user feedback system for a user of a delivery device (10) within a delivery ecosystem (1) comprises a sensor platform (215) comprising at least a first sensor operable to detect at least a first physical property associated with at least one of user behavior other than inhalation and user physiology other than in relation to inhalation, as described elsewhere herein.

It will be appreciated that a physical property associated with user behavior other than inhalation optionally comprise interactions of the user with one or more devices within the delivery ecosystem (typically the delivery device) that do not include the actual act of inhalation on the delivery device, as described elsewhere herein; and may optionally comprise other actions and behaviors of the user such as their overall movement, facial expression, vocalization, etc., that may be relevant to their state.

Similarly a physical property associated with user physiology other than in relation to inhalation comprises physiological measurements other than those relating to inhalation (which may include breathing rate, airflow rate and the like). Hence the physiological measurements may relate to those measurable using physical contact, typically physical contact with electrodes, typically by the user's hand, as described elsewhere herein, such as galvanic skin response, heart rate, muscle tension, and the like, or using other sensors such as for example to detect cortisol levels in saliva or sweat.

In addition, the user feedback system comprises an obtaining processor (1010) adapted to output data based upon the or each detected physical property as all or part of a user factor indicative of a user state, as described elsewhere herein; and an estimation processor (1020) adapted to identify a corresponding feedback action expected to alter a state of the user as indicated at least in part by the or each detected physical property, as described elsewhere herein.

In an instance of this summary embodiment, a feedback processor (1030) adapted to select at least a first feedback action identified by the estimation processor for at least a first device within the delivery ecosystem, as described elsewhere herein.

In this case, the feedback processor may optionally be adapted to cause a modification of one or more operations of at least a first device within the delivery ecosystem according to the or each selected feedback action, as described elsewhere herein. In this case, furthermore the device within the delivery ecosystem for which one or more operations is modified is optionally the delivery device (10), as described elsewhere herein.

In an instance of the summary embodiment, the sensor platform comprises one or more selected from the list consisting of a motion sensor, a camera, a microphone, and a pressure or force sensor, as described elsewhere herein.

In a case of this instance, a motion sensor may be operable to detect one or more a physical properties selected from the list consisting of small involuntary movements of the user's hand, localized reorientation/rotation of the delivery device, movement of the delivery device into an engagement position with the user's mouth, a pendulum motion, vertical motion (e.g. up stairs), and horizontal motion (e.g. walking or driving), as described elsewhere herein.

In a case of this instance, a camera may be operable to detect one or more physical properties selected from the list consisting of facial expression, muscle tension, eye movement, motion of the camera, whether the user is indoors or outdoors, and the presence of other people, as described elsewhere herein.

In a case of this instance, a microphone may be operable to detect one or more physical properties selected from the list consisting of the volume of the user's voice, word speed, timbre, pitch, non-harmonic content, and keywords, as described elsewhere herein.

In a case of this instance, a pressure or force sensor may be operable to detect one or more physical properties selected from the list consisting of a peak pressure or force applied to a user interface element, and a pressure or force profile during a user interaction, as described elsewhere herein.

Instance of the summary embodiment, the sensor platform comprises one or more selected from the list consisting of a galvanic skin response sensor, a heart rate sensor, a muscle tension sensor, and a touch sensor, as described elsewhere herein.

In this case, optionally the or each detector is located on one or more selected from the list consisting of a grip portion of the delivery device, a mouthpiece of the delivery device, and an activation button of the delivery device, as described elsewhere herein.

Similarly in this case optionally the sensor platform comprises electrodes for detecting a physical property of the user that are shared by two or more sensors, as described elsewhere herein.

In an instance of the summary embodiment, the sensor platform comprises a cortisol sensor, as described elsewhere herein.

In an instance of the summary embodiment, the sensor platform is located at least in part on one or more selected from the list consisting of the delivery device (10), a mobile phone (100), a docking station for the delivery device (200), and a wearable fitness device (400), as described elsewhere herein.

In an instance of the summary embodiment, the sensor platform comprises a sensor operable to measure two or more physical properties, as described elsewhere herein.

In an instance of the summary embodiment, a user interface is operable to receive an indication of user state from the user, as described elsewhere herein.

In an instance of the summary embodiment, one or more further obtained user factors respectively relate to at least one class selected from the list consisting of historical data providing background information relating to the user neurological data relating to the user, physiological data relating to the user, contextual data relating to the user, environmental data relating to the user, and deterministic data relating to the user, as described elsewhere herein.

In an instance of the summary embodiment, the obtaining processor generates inputs for the estimation processor comprising one or more selected from the list consisting of one or more individual values based upon one or more respective user factors, one or more combined values based upon two or more respective user factors, and one or more values based upon respective user factors from a single class of data, as described elsewhere herein.

In an instance of the summary embodiment, the estimation processor is operable to calculate an estimate of the user state as one or more selected from the list consisting of a single representative value, a representative category, and a multivariate representation, as described elsewhere herein.

In an instance of the summary embodiment, the estimation processor is operable to identify one or more proposed feedback actions based upon the one or more of the obtained user factors, as described elsewhere herein.

In this case, optionally the estimation processor does not generate an explicit estimation of user state as an interim operation in the identification of the one or more proposed feedback actions, as described elsewhere herein.

In an instance of the summary embodiment, the estimation processor is operable to identify one or more proposed feedback actions relating to one or more selected from the list consisting of a behavioral feedback action for affecting at least a first behavior of the user, a pharmaceutical feedback action for affecting the consumption of an active ingredient by the user, and a non-consumption feedback action for affecting one or more non-consumption operations of the delivery ecosystem, as described elsewhere herein.

In an instance of the summary embodiment, the delivery ecosystem comprises one or more selected from the list consisting of one or more delivery devices (10), one or more mobile terminals (100), one or more wearable devices (400), and one or more docking units (200) for the or each delivery device, as described elsewhere herein.

In an instance of the summary embodiment, functionality of one or more of the obtaining processor, estimation processor, and a feedback processor is provided at least in part by a remote server (1000), as described elsewhere herein.

In an instance of the summary embodiment, functionality of one or more of the obtaining processor, estimation processor, and a feedback processor is provided at least in part by one or more processors located within one or more devices (10, 100, 200, 300, 400) of the delivery ecosystem (1).

Figure 7:
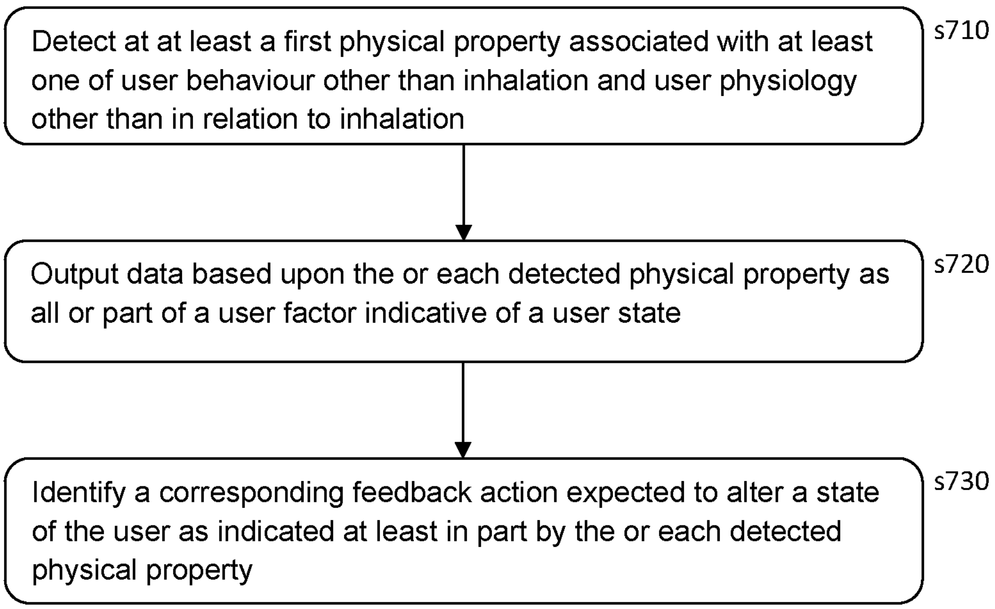
FIG. 7 is a flow diagram of a user feedback method for a user of a delivery device within a delivery ecosystem, in accordance with embodiments of the description.

Turning now to FIG. 7, in a summary embodiment of the present description, a user feedback method for a user of a delivery device within a delivery ecosystem comprises the following operations.

Detecting at s710 comprises detecting, using at least a first sensor of a sensor platform (215), at least a first physical property associated with at least one of user behavior other than inhalation and user physiology other than in relation to inhalation as described elsewhere herein.

In a similar manner to the previous summary embodiment, it will be appreciated that a physical property associated with user behavior other than inhalation optionally comprise interactions of the user with one or more devices within the delivery ecosystem (typically the delivery device) that do not include the actual act of inhalation on the delivery device, as described elsewhere herein; and may optionally comprise other actions and behaviors of the user such as their overall movement, facial expression, vocalization, etc., that may be relevant to their state. Similarly a physical property associated with user physiology other than in relation to inhalation comprises physiological measurements other than those relating to inhalation (which may include breathing rate, airflow rate and the like). Hence the physiological measurements may relate to those measurable using physical contact, typically physical contact with electrodes, typically by the user's hand, as described elsewhere herein, such as galvanic skin response, heart rate, muscle tension, and the like, or using other sensors such as for example to detect cortisol levels in saliva or sweat.

Meanwhile, outputting at s720 comprises outputting data based upon the or each detected physical property as all or part of a user factor indicative of a user state, as described elsewhere herein.

Then estimating at s730 comprises identifying a corresponding feedback action expected to alter a state of the user as indicated at least in part by the or each detected physical property, as described elsewhere herein.

It will be apparent to a person skilled in the art that variations in the above method corresponding to operation of the various embodiments of the method and/or apparatus as described and claimed herein are considered within the scope of the present disclosure, including but not limited to:

- an operation of selecting an feedback action identified by the estimation processor for at least a first device within the delivery ecosystem, as described elsewhere herein;
  - in this case, optionally a operation of causing a modification of one or more operations of at least a first device within the delivery ecosystem according to the selected feedback action, as described elsewhere herein; and
    - in this case, optionally the at least first device within the delivery ecosystem for which one or more operations is modified is the delivery device (10), as described elsewhere herein;
- the sensor platform comprising one or more selected from the list consisting of a motion sensor, a camera, a microphone, and a pressure or force sensor, as described elsewhere herein;
  - a motion sensor being optionally operable to detect one or more a physical properties selected from the list consisting of small involuntary movements of the user's hand, localized reorientation/rotation of the delivery device, movement of the delivery device into an engagement position with the user's mouth, a pendulum motion, vertical motion (e.g. up stairs), and horizontal motion (e.g. walking or driving), as described elsewhere herein;
  - a camera being optionally operable to detect one or more physical properties selected from the list consisting of facial expression, muscle tension, eye movement, motion of the camera, whether the user is indoors or outdoors, and the presence of other people, as described elsewhere herein;
  - a microphone being optionally operable to detect one or more physical properties selected from the list consisting of the volume of the user's voice, word speed, timbre, pitch, non-harmonic content, and keywords, as described elsewhere herein;
  - a pressure or force sensor being optionally operable to detect one or more physical properties selected from the list consisting of a peak pressure or force applied to a user interface element, and a pressure or force profile during a user interaction, as described elsewhere herein;

the sensor platform comprising one or more selected from the list consisting of a galvanic skin response sensor, a heart rate sensor, a muscle tension sensor, and a touch sensor, as described elsewhere herein;

in this case, the or each detector optionally being located on one or more selected from the list consisting of a grip portion of the delivery device, a mouthpiece of the delivery device, and an activation button of the delivery device, as described elsewhere herein;

similarly in this case the sensor platform optionally comprising electrodes for detecting a physical property of the user that are shared by two or more sensors, as described elsewhere herein;

the sensor platform comprising a cortisol sensor, as described elsewhere herein;

the sensor platform being located at least in part on one or more selected from the list consisting of the delivery device (10), a mobile phone (100), a docking station for the delivery device (200), and a wearable fitness device (400), as described elsewhere herein;

a sensor platform comprising a sensor operable to measure two or more physical properties, as described elsewhere herein;

providing a user interface operable to receive an indication of user state from the user, as described elsewhere herein;

one or more further obtained user factors respectively relating to at least one class selected from the list consisting of historical data providing background information relating to the user neurological data relating to the user, physiological data relating to the user, contextual data relating to the user, environmental data relating to the user, and deterministic data relating to the user, as described elsewhere herein;

the obtaining operation generating inputs for the estimation processor comprising one or more selected from the list consisting of one or more individual values based upon one or more respective user factors, one or more combined values based upon two or more respective user factors, and one or more values based upon respective user factors from a single class of data, as described elsewhere herein;

the estimation operation comprising calculating an estimate of the user state as one or more selected from the list consisting of a single representative value, a representative category, and a multivariate representation, as described elsewhere herein;

the estimation operation comprising identifying one or more proposed feedback actions based upon the one or more of the obtained user factors, as described elsewhere herein;

in this case, optionally the estimation operation does not generate an explicit estimation of user state as an interim operation in the identification of the one or more proposed feedback actions, as described elsewhere herein;

the estimation operation comprising identifying one or more proposed feedback actions relating to one or more selected from the list consisting of a behavioral feedback action for affecting at least a first behavior of the user, a pharmaceutical feedback action for affecting the consumption of an active ingredient by the user, and a non-consumption feedback action for affecting one or more non-consumption operations of the delivery ecosystem, as described elsewhere herein;

a feedback operation in turn comprising the operations of selecting a feedback action identified by the estimation operation for at least a first device within the delivery ecosystem, and selecting which device within the delivery ecosystem will implement a respective selected proposed feedback action, as described elsewhere herein;

the delivery ecosystem comprising one or more selected from the list consisting of one or more delivery devices (10), one or more mobile terminals (100), one or more wearable devices (400), and one or more docking units (200) for the or each delivery device, as described elsewhere herein;

the functionality of one or more of the obtaining operation, estimation operation, and feedback operation is provided at least in part by a remote server (1000), as described elsewhere herein;

the functionality of one or more of the obtaining operation, estimation operation, and feedback operation is provided at least in part by one or more processors located within one or more devices (10, 100, 200, 300, 400) of the delivery ecosystem (1); and in an instance of the summary embodiment, the one or more user factors include one or more user factors selected from the group comprising: one or more user inhalation characteristics, output from one or more motion sensors configured to detect micromovements or tremors of a user, and the output from one or more sensors configured to detect when and/or how a user is holding a device of the delivery ecosystem, as described elsewhere herein.

It will be appreciated that the above methods may be carried out on conventional hardware (such as the obtaining processor, estimation processor feedback processor, on the server and/or any one of the devices of the delivery ecosystem) suitably adapted as applicable by software instruction or by the inclusion or substitution of dedicated hardware.

Thus the required adaptation to existing parts of a conventional equivalent device may be implemented in the form of a computer program product comprising processor implementable instructions stored on a non-transitory machine-readable medium such as a floppy disk, optical disk, hard disk, solid state disk, PROM, RAM, flash memory or any combination of these or other storage media, or realized in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these or other networks.

The invention claimed is:

1. A user feedback system for a user of a delivery device within a delivery ecosystem, comprising:

a sensor platform comprising at least a first sensor operable to detect at least a first physical property associated with at least one of a user behaviour other than inhalation and a user physiology other than in relation to inhalation, wherein the at least a first sensor is a pressure or force sensor operable to detect one or more physical properties selected from the group consisting of: a peak pressure or a peak force applied to a user interface element; and a pressure or a force profile during a user interaction;

an obtaining processor adapted to output data based upon the detected at least first physical property as all or part of a user factor indicative of a user state;

an estimation processor adapted to identify a corresponding feedback action expected to alter the state as indicated by the user factor; and a feedback processor adapted to select at least a first feedback action identified by the estimation processor for at least a first device within the delivery ecosystem, wherein the feedback processor is adapted to cause a modification of one or more operations of at least the first device within the delivery ecosystem according to the selected at least first feedback action.

2. The user feedback system according to claim 1, wherein the device within the delivery ecosystem for which one or more operations is modified is the delivery device.

3. The user feedback system according to claim 1, wherein the sensor platform comprises one or more selected from the group consisting of:

a motion sensor;

a camera; and a microphone.

4. The user feedback system according to claim 3, wherein the motion sensor is operable to detect one or more physical properties selected from the group consisting of:

small involuntary movements of a hand of the user;

localized reorientation or rotation of the delivery device;

movement of the delivery device into an engagement position with a mouth of the user;

a pendulum motion;

vertical motion; and horizontal motion.

5. The user feedback system according to claim 3, wherein the camera is operable to detect one or more physical properties selected from the group consisting of:

a facial expression;

a muscle tension;

an eye movement;

a motion of the camera;

whether the user is indoors or outdoors; and a presence of other people.

6. The user feedback system according to claim 3, wherein the microphone is operable to detect one or more physical properties selected from the group consisting of:

a volume of a voice of the user;

a word speed;

a timbre;

a pitch;

non-harmonic content; and keywords.

7. The user feedback system according to claim 1, wherein the sensor platform comprises one or more selected from the group consisting of:

a galvanic skin response sensor;

a heart rate sensor;

a muscle tension sensor; and a touch sensor.

8. The user feedback system according to claim 7, wherein the at least first sensor is located on one or more selected from the group consisting of:

a grip portion of the delivery device;

a mouthpiece of the delivery device; and an activation button of the delivery device.

9. The user feedback system according to claim 7, wherein the sensor platform comprises electrodes for detecting a physical property of the user and the electrodes are shared by two or more sensors.

10. The user feedback system according to claim 1, wherein the sensor platform comprises a cortisol sensor.

11. The user feedback system according to claim 1, wherein the sensor platform is located at least in part on one or more selected from the group consisting of:

the delivery device;

a mobile phone;

a docking station for the delivery device; and a wearable fitness device.

12. The user feedback system according to claim 1, wherein the sensor platform comprises a sensor operable to measure two or more physical properties.

13. The user feedback system according to claim 1, further comprising a user interface operable to receive an indication of the user state from the user.

14. The user feedback method according to claim 13, wherein the estimating comprises identifying one or more proposed feedback actions based upon the one or more obtained user factors.

15. The user feedback system according to claim 1, wherein one or more further obtained user factors respectively relate to at least one class selected from the group consisting of:

historical data providing background information relating to the user;

neurological data relating to the user;

physiological data relating to the user;

contextual data relating to the user;

environmental data relating to the user; and deterministic data relating to the user.

16. The user feedback system according to claim 1, wherein the obtaining processor generates inputs for the estimation processor comprising one or more selected from the group consisting of:

one or more individual values based upon one or more respective user factors;

one or more combined values based upon two or more respective user factors; and one or more values based upon respective user factors from a single class of data.

17. The user feedback system according to claim 1, wherein the estimation processor is operable to calculate an estimate of the user state as one or more selected from the group consisting of:

a single representative value;

a representative category; and a multivariate representation.

18. The user feedback system according to claim 1, wherein the estimation processor is operable to identify one or more proposed feedback actions based upon the one or more obtained user factors.

19. The user feedback system according to claim 18, wherein the estimation processor does not generate an explicit estimation of user state as an interim operation in the identification of the one or more proposed feedback actions.

20. The user feedback system according to claim 1, wherein the estimation processor is operable to identify one or more proposed feedback actions relating to one or more selected from the group consisting of:

a behavioral feedback action for affecting at least a first behavior of the user;

a pharmaceutical feedback action for affecting consumption of an active ingredient by the user; and a non-consumption feedback action for affecting one or more non-consumption operations of the delivery ecosystem.

21. The user feedback system according to claim 1, wherein the delivery ecosystem comprises one or more selected from the group consisting of:

one or more delivery devices;

one or more mobile terminals;

one or more wearable devices; and one or more docking units for the one or more delivery devices.

22. The user feedback system according to claim 1, wherein functionality of one or more of the obtaining processor, the estimation processor, or a feedback processor is provided at least in part by a remote server.

23. The user feedback system according to claim 1, wherein functionality of one or more of the obtaining processor, the estimation processor, and a feedback processor is provided at least in part by one or more processors located within one or more devices of the delivery ecosystem.

24. A user feedback method for a user of a delivery device within a delivery ecosystem comprising:

detecting, using at least a first sensor of a sensor platform, at least a first physical property associated with at least one of user behavior other than inhalation and user physiology other than in relation to inhalation, wherein the at least a first sensor is a pressure or force sensor operable to detect one or more physical properties selected from the group consisting of: a peak pressure or a peak force applied to a user interface element; and a pressure or a force profile during a user interaction;

outputting data based upon the detected at least first physical property as all or part of a user factor indicative of a user state;

estimating by identifying a corresponding feedback action expected to alter a user state as indicated by the user factor;

selecting a feedback action identified in the estimating for at least a first device within the delivery ecosystem; and causing a modification of one or more operations of at least a first device within the delivery ecosystem according to the selected feedback action.

25. The user feedback method according to claim 24, the at least first device within the delivery ecosystem for which one or more operations is modified is the delivery device.

26. The user feedback method according to claim 24, wherein the sensor platform comprises one or more selected from the group consisting of:

a motion sensor;

a camera;

a microphone; and a pressure sensor or a force sensor.

27. The user feedback method according to claim 24, wherein the sensor platform comprises one or more selected from the group consisting of:

a galvanic skin response sensor;

a heart rate sensor;

a muscle tension sensor; and a touch sensor.

28. The user feedback method according to claim 27, wherein the sensor platform comprises electrodes for detecting a physical property of the user and the electrodes are shared by two or more sensors.

29. The user feedback method according to claim 24, wherein the sensor platform comprises a cortisol sensor.

30. The user feedback method according to claim 24, wherein the sensor platform is located at least in part on one or more selected from the group consisting of:

the delivery device;

a mobile phone;

a docking station for the delivery device; and a wearable fitness device.

31. The user feedback method according to claim 24, wherein the sensor platform comprises a sensor operable to measure two or more physical properties.

32. The user feedback method according to claim 24, wherein the estimating comprises identifying the one or more proposed feedback actions without generating an explicit estimation of user state as an interim operation.

33. The user feedback method according to claim 24, wherein the estimating comprises identifying one or more proposed feedback actions relating to one or more selected from the group consisting of:

a behavioral feedback action for affecting at least a first behavior of the user;

a pharmaceutical feedback action for affecting consumption of an active ingredient by the user; and a non-consumption feedback action for affecting one or more non-consumption operations of the delivery ecosystem.

34. The user feedback method according to claim 24, further comprising feedback comprising:

selecting a feedback action identified by the estimating for at least a first device within the delivery ecosystem; and selecting which device within the delivery ecosystem will implement a respective selected proposed feedback action.

35. A computer system comprising at least one processor and memory configured to perform the method of claim 24.

* * * * *